(12) United States Patent
Ameri et al.

(10) Patent No.: US 7,579,013 B2
(45) Date of Patent: Aug. 25, 2009

(54) FORMULATIONS FOR COATED MICROPROJECTIONS CONTAINING NON-VOLATILE COUNTERIONS

(75) Inventors: Mahmoud Ameri, Fremont, CA (US); WeiQi Lin, Palo Alto, CA (US); Michel J. N. Cormier, Mountain View, CA (US); Yuh-Fun Maa, Millbrae, CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 10/880,702

(22) Filed: Jun. 29, 2004

(65) Prior Publication Data

US 2004/0265354 A1 Dec. 30, 2004

Related U.S. Application Data

(60) Provisional application No. 60/484,020, filed on Jun. 30, 2003.

(51) Int. Cl.
 A61K 9/00 (2006.01)
 C07K 14/00 (2006.01)
(52) U.S. Cl. .............................. 424/400; 514/2; 530/300
(58) Field of Classification Search ........................ None
 See application file for complete search history.

(56) References Cited

U.S. PATENT DOCUMENTS

| | | | |
|---|---|---|---|
| 2,619,962 A | 12/1952 | Rosenthal | |
| 2,893,392 A | 7/1959 | Wagner et al. | |
| 3,072,122 A | 1/1963 | Rosenthal | |
| 3,123,212 A | 3/1964 | Taylor et al. | |
| 3,136,314 A | 6/1964 | Kravitz | |
| RE25,637 E | 9/1964 | Kravitz et al. | |
| 3,221,739 A | 12/1965 | Rosenthal | |
| 3,221,740 A | 12/1965 | Rosenthal | |
| 3,678,150 A | 7/1972 | Szumski et al. | |
| 3,814,097 A | 6/1974 | Ganderton et al. | |
| 3,964,482 A | 6/1976 | Gerstel et al. | |
| 4,109,655 A | 8/1978 | Chacornac | |
| 4,453,926 A | 6/1984 | Galy | |
| 4,714,621 A | 12/1987 | Gullberg et al. | |
| 5,066,494 A | 11/1991 | Becher | |
| 5,250,023 A | 10/1993 | Lee et al. | |
| 5,279,544 A | 1/1994 | Gross et al. | |
| 5,487,726 A | 1/1996 | Rabenau et al. | |
| 5,738,728 A | 4/1998 | Tisone | |
| 5,741,554 A | 4/1998 | Tisone | |
| 5,743,960 A | 4/1998 | Tisone | |
| 5,770,220 A | 6/1998 | Meconi et al. | |
| 5,866,536 A * | 2/1999 | Leone-Bay et al. ............ 514/2 | |
| 5,879,326 A | 3/1999 | Godshell et al. | |
| 5,916,524 A | 6/1999 | Tisone | |
| 5,983,136 A | 11/1999 | Kamen | |
| 6,050,988 A | 4/2000 | Zuck | |
| 6,083,196 A | 7/2000 | Trautman et al. | |
| 6,091,975 A | 7/2000 | Daddona et al. | |
| 6,230,051 B1 | 5/2001 | Cormier et al. | |
| 6,322,808 B1 | 11/2001 | Trautman et al. | |
| 6,331,310 B1 | 12/2001 | Roser et al. | |
| 6,379,324 B1 | 4/2002 | Gartstein et al. | |
| 6,440,096 B1 | 8/2002 | Lastovich et al. | |
| 6,454,755 B1 | 9/2002 | Godshall | |
| 6,537,242 B1 | 3/2003 | Palmer | |
| 6,565,532 B1 | 5/2003 | Yuzhakov et al. | |
| 6,589,202 B1 | 7/2003 | Powell | |
| 6,652,478 B1 | 11/2003 | Gartstein et al. | |
| 6,689,100 B2 | 2/2004 | Connelly et al. | |
| 6,743,211 B1 | 6/2004 | Prausnitz et al. | |
| 6,811,792 B2 | 11/2004 | Roser et al. | |
| 6,835,184 B1 | 12/2004 | Sage et al. | |
| 6,855,131 B2 | 2/2005 | Trautman et al. | |
| 6,855,372 B2 | 2/2005 | Trautman et al. | |
| 6,881,203 B2 | 4/2005 | Delmore | |
| 6,884,427 B1 | 4/2005 | Barrows | |
| 6,918,901 B1 | 7/2005 | Theeuwes et al. | |
| 6,931,277 B1 | 8/2005 | Yuzhakov et al. | |
| 6,953,589 B1 | 10/2005 | Trautman et al. | |
| 7,097,631 B2 | 8/2006 | Trautman et al. | |
| 7,131,960 B2 | 11/2006 | Trautman et al. | |
| 7,184,826 B2 | 2/2007 | Cormier et al. | |
| 2002/0082543 A1 | 6/2002 | Park et al. | |
| 2002/0087182 A1 | 7/2002 | Trautman et al. | |

(Continued)

FOREIGN PATENT DOCUMENTS

EP  0407063  6/1990

(Continued)

OTHER PUBLICATIONS

Suzuki et al. Journal of Pharmaceutical Sciences 91(2): 350-361 (2002). "Prevention of Bone Loss in Ovariectomized Rats by Pulsatile Transdermal Iontophorectic Administration of Human PTH(1-34)".*
Edsall J.T., Proteins as Acids and Bases, 20:444-505, (1943).
International Search Report dated Mar. 2, 2005 for corresponding Appn. PCT/US2004/021004.
Gorukanti, et al. Transdermal delivery of antiparkinsonian agent, benztropine. I. Effect of vehicles on skin permeation. Int J Pharm. 1999; 192(2):159-72.
Hatanaka, et al. Ion pair skin transport of a zwitterionic drug, cephalexin. J Control Release. 2000; 66(1):63-71.

(Continued)

Primary Examiner—Anand U Desai
(74) Attorney, Agent, or Firm—Edwards Angell Palmer & Dodge LLP; Kathleen Williams

(57) ABSTRACT

The invention provides for a formulation for coating one or more microprojections which reduces or minimizes the loss of counterions from the coating in order to achieve a pH-stabilized formulation.

15 Claims, 6 Drawing Sheets

U.S. PATENT DOCUMENTS

| | | | |
|---|---|---|---|
| 2002/0128599 A1 | 9/2002 | Cormier et al. | |
| 2002/0132054 A1 | 9/2002 | Trautman et al. | |
| 2002/0177839 A1 | 11/2002 | Cormier et al. | |
| 2002/0193729 A1 | 12/2002 | Cormier et al. | |
| 2003/0100885 A1 | 5/2003 | Pettis et al. | |
| 2003/0135201 A1 | 7/2003 | Gonnelli | |
| 2003/0181936 A1 | 9/2003 | Trautman et al. | |
| 2003/0199810 A1 | 10/2003 | Trautman et al. | |
| 2003/0199811 A1 | 10/2003 | Sage, Jr. et al. | |
| 2004/0062813 A1 | 4/2004 | Cormier et al. | |
| 2004/0138610 A1* | 7/2004 | Cormier et al. | 604/46 |
| 2004/0236271 A1 | 11/2004 | Theeuwes et al. | |
| 2005/0008683 A1 | 1/2005 | Mikszta et al. | |
| 2005/0084604 A1 | 4/2005 | Trautman et al. | |
| 2005/0106209 A1 | 5/2005 | Ameri et al. | |
| 2005/0123507 A1 | 6/2005 | Ameri | |
| 2005/0148926 A1 | 7/2005 | Trautman et al. | |
| 2006/0047243 A1 | 3/2006 | Rosenberg | |
| 2006/0074377 A1 | 4/2006 | Cormier et al. | |
| 2006/0188555 A1* | 8/2006 | Cormier et al. | 424/448 |

FOREIGN PATENT DOCUMENTS

| | | |
|---|---|---|
| EP | 1110455 A | 6/2001 |
| EP | 1283043 A | 2/2003 |
| EP | 1 358 896 | 11/2003 |
| EP | 1 517 722 | 3/2005 |
| GB | 0017999.4 | 5/1922 |
| GB | 878788 | 10/1961 |
| WO | 96/03978 | 2/1996 |
| WO | 96/10630 | 4/1996 |
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/48442 | 6/1997 |
| WO | 97/48440 | 12/1997 |
| WO | WO 97/48440 | 12/1997 |
| WO | WO 97/48441 | 12/1997 |
| WO | WO 98/00193 | 1/1998 |
| WO | WO 98/11937 | 3/1998 |
| WO | 98/28037 | 7/1998 |
| WO | WO 98/28037 | 7/1998 |
| WO | WO 98/29298 | 7/1998 |
| WO | WO 98/29365 | 7/1998 |
| WO | WO 99/38492 A | 8/1999 |
| WO | 99/64580 | 12/1999 |
| WO | WO 99/64580 | 12/1999 |
| WO | 00/12173 | 3/2000 |
| WO | WO 00/21533 A | 4/2000 |
| WO | 00/35530 | 6/2000 |
| WO | WO 00/37079 A | 6/2000 |
| WO | WO 00/43405 A | 7/2000 |
| WO | 00/44438 | 8/2000 |
| WO | WO 01/41863 A | 6/2001 |
| WO | 02/07813 | 1/2002 |
| WO | WO 02/00200 A | 1/2002 |
| WO | WO 02/07813 | 1/2002 |
| WO | 02/074173 | 9/2002 |
| WO | WO 02/085447 A | 10/2002 |
| WO | WO 02/094368 A | 11/2002 |
| WO | 1 301 238 | 4/2003 |
| WO | WO 03/051284 A | 6/2003 |
| WO | WO 2005/002453 A | 1/2005 |
| WO | WO 2005/004729 A | 1/2005 |

OTHER PUBLICATIONS

Valenta, et al. The dermal delivery of lignocaine: influence of ion pairing. Int J Pharm. 2000; 197(1-2):77-85.

Gribbon, et al., "Stabilisation of Vaccines Using trehalose (Q-T4) Technology", Brown F(ed); New Approaches to Stabilation of Vaccines Potency, Dev Biol Stand. Basel, Karger, 1996; vol. 87; pp. 193-199.

Franks, "Solid aqueous solutions"; Pure & Appl. Chem.; vol. 65; No. 12; 1993; pp. 2527-2537.

Coleco et al.; Research/"Extraordinary Stability of Enzymes Dried in Trehalose: Simplified Molecular Biology"; bio/Technology; vol. 10; Sep. 1992; pp. 1007-1011.

"Report of the Technical Review Group Meeting"; WHO, Jun. 7-8, 1999; pp. 1-88.

"A plethora of hi-tech vaccines-genetic, edible, sugar glass, and more"; Children's Vaccine Initiative; CVI Forum 18; 1999; pp. 1-24.

"Report on the first meeting of the steering committee on Immunization Safety"; WHO Geneva; Oct. 25-26, 1999; pp. 1-44.

Roberts, et al.; "Solute Structure as a Determinant of Iontophoretic Transport"; Mechanisms of Transdermal Drug Delivery; R. O. Potts and R. H. Guy (Ed); Marcel Dekker (1997); pp. 291-349.

Chang, et al.; "Use of Subambient Thermal Analysis to Optimize Protein Lyophilization"; Cryobiology 29; (1992); pp. 632-656.

Wang, "Lyophilzation and development of solid protein pharmaceuticals"; International Journal of Pharmaceutics; 203; (2000); pp. 1-60.

Carpenter, et al.; "Rational Design of Stable Lyophilized Protein Formulations: Some Practical Advice"; Pharmaceutical Research; vol. 14; No. 8; 1997; pp. 969-975.

Huang, et al.; "Microencapsulation for Gene Delivery"; Encyclopedia of Controlled Drug Delivery; John Wiley & Sons, Inc.; (1999); pp. 546-553.

General Policy Issues, "Wider access to HIV drugs now a reality"; WHO Drug Information; vol. 12; No. 2; 1998; pp. 67-99.

Roos; "Melting and glass transitions of low molecular weight carbohydrates"; Carbohydrate Research; 238; (1993); pp. 39-48.

Schunk et al.; "Liquid film coating"; Scientific principles and their technological implications; Kistler and Schweizer; Editors; Chapan & Hall; London; (1997); pp. 673-708.

"HIV/PPD Conjugate Vaccine Active in Clinical Trial" (1998).

"Glass pharmacy"; New Science Publications; Mar. 8, 1997; pp. 24-27.

Fox; "Putting Proteins Under Glass"; Science; vol. 267; Mar. 31, 1999; pp. 1922-1923.

Henry et al.; "Microfabricated Microneedles: A Novel Approach to Transdermal Drug Delivery"; Journal of Pharmaceutical Sciences; vol. 87; No. 8; Aug. 1998; pp. 922-925.

Rola, Ph. D.; "Immunizing Agents and Diagnostic Skin Antigens"; Remington's 17th Edition; Pharmaceutical Sciences; (1985); pp. 1380-1395; Mack Publishing Company; Pennsylvania.

* cited by examiner

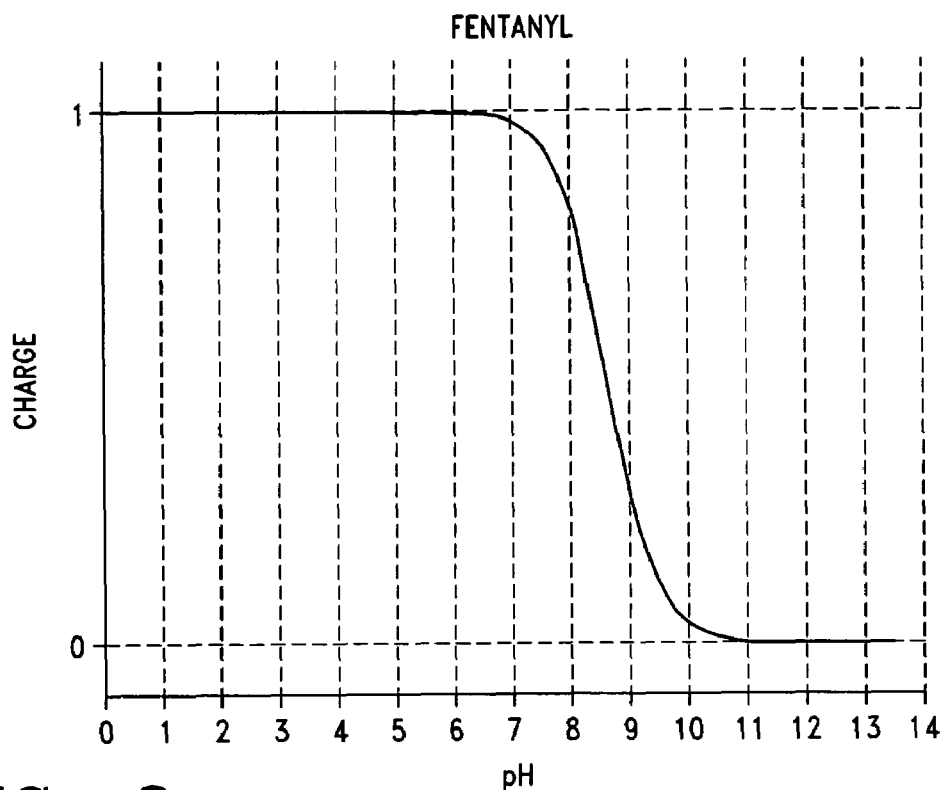
FIG.−3
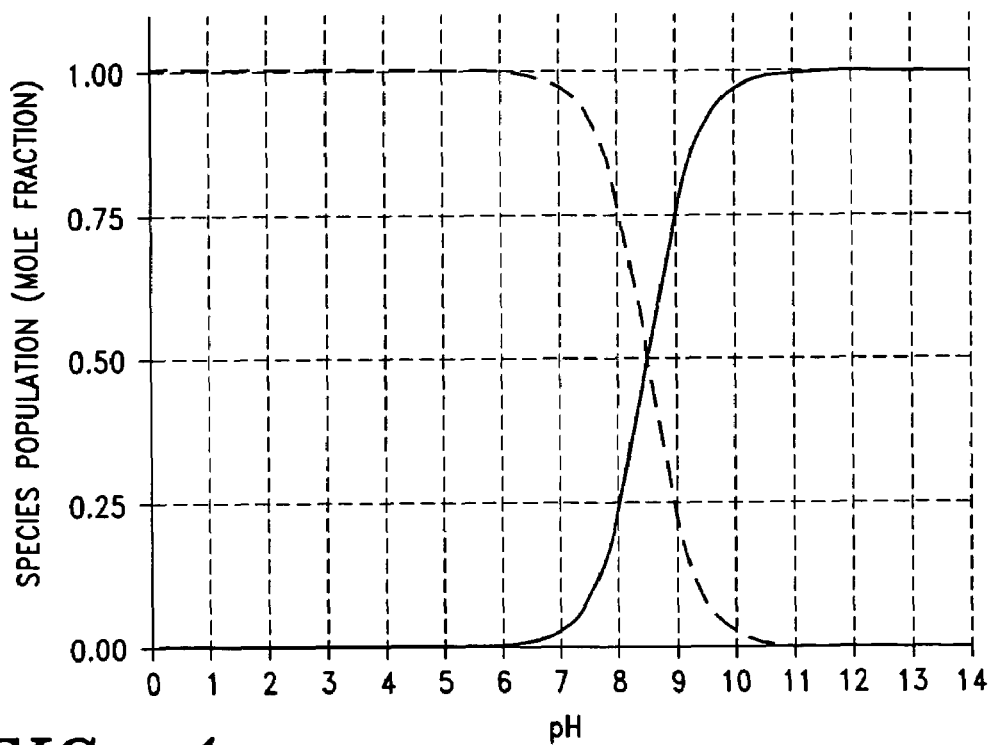
FIG.−4

FORMULATIONS FOR COATED MICROPROJECTIONS CONTAINING NON-VOLATILE COUNTERIONS

This application claims the benefit of U.S. Provisional Application No. 60/484,020, filed Jun. 30, 2003.

FIELD OF THE PRESENT INVENTION

This invention relates to administering and enhancing the transdermal delivery of an agent across the skin. More particularly, the invention relates to a percutaneous drug delivery system for administering a biologically active agent through the stratum corneum using skin piercing microprojections which have a dry coating of the biologically active agent. Delivery of the agent is achieved when the microprojections pierce the skin of a patient and the patient's interstitial fluid contacts and dissolves the active agent. More specifically it relates to a coating formulation which resists changes in the pH of the coating and promotes the solubilization of the coating after the microprojections have pierced the skin.

BACKGROUND OF THE INVENTION

Drugs are most conventionally administered either orally or by injection. Unfortunately, many medicaments are completely ineffective or have radically reduced efficacy when orally administered since they either are not absorbed or are adversely affected before entering the bloodstream and thus do not possess the desired activity. On the other hand, the direct injection of the medicament into the bloodstream, while assuring no modification of the medicament during administration, is a difficult, inconvenient, painful and uncomfortable procedure, sometimes resulting in poor patient compliance.

Hence, in principle, transdermal delivery provides for a method of administering drugs that would otherwise need to be delivered via hypodermic injection or intravenous infusion. Transdermal drug delivery offers improvements in both of these areas. Transdermal delivery when compared to oral delivery avoids the harsh environment of the digestive tract, bypasses gastrointestinal drug metabolism, reduces first-pass effects, and avoids the possible deactivation by digestive and liver enzymes. Conversely, the digestive tract is not subjected to the drug during transdermal administration. Indeed, many drugs such as aspirin have an adverse effect on the digestive tract. However, in many instances, the rate of delivery or flux of many agents via the passive transdermal route is too limited to be therapeutically effective.

The word "transdermal" is used herein as a generic term referring to passage of an agent across the skin layers. The word "transdermal" refers to delivery of an agent (e.g., a therapeutic agent such as a drug) through the skin to the local tissue or systemic circulatory system without substantial cutting or piercing of the skin, such as cutting with a surgical knife or piercing the skin with a hypodermic needle. Transdermal agent delivery includes delivery via passive diffusion as well as by external energy sources including electricity (e.g., iontophoresis) and ultrasound (e.g., phonophoresis). While drugs do diffuse across both the stratum corneum and the epidermis, the rate of diffusion through the stratum corneum is often the limiting step. Many compounds, in order to achieve a therapeutic dose, require higher delivery rates than can be achieved by simple passive transdermal diffusion. When compared to injections, transdermal agent delivery eliminates the associated pain and reduces the possibility of infection.

Theoretically, the transdermal route of agent administration could be advantageous in the delivery of many therapeutic proteins, because proteins are susceptible to gastrointestinal degradation and exhibit poor gastrointestinal uptake and transdermal devices are more acceptable to patients than injections. However, the transdermal flux of medically useful peptides and proteins is often insufficient to be therapeutically effective due to the large size/molecular weight of these molecules. Often the delivery rate or flux is insufficient to produce the desired effect or the agent is degraded prior to reaching the target site, for example while in the patient's bloodstream.

Transdermal drug delivery systems generally rely on passive diffusion to administer the drug while active transdermal drug delivery systems rely on an external energy source (e.g., electricity) to deliver the drug. Passive transdermal drug delivery systems are more common. Passive transdermal systems have a drug reservoir containing a high concentration of drug adapted to contact the skin where the drug diffuses through the skin and into the body tissues or bloodstream of a patient. The transdermal drug flux is dependent upon the condition of the skin, the size and physical/chemical properties of the drug molecule, and the concentration gradient across the skin. Because of the low permeability of the skin to many drugs, transdermal delivery has had limited applications. This low permeability is attributed primarily to the stratum corneum, the outermost skin layer which consists of flat, dead cells filled with keratin fibers (keratinocytes) surrounded by lipid bilayers. This highly-ordered structure of the lipid bilayers confers a relatively impermeable character to the stratum corneum.

Active transport systems use an external energy source to assist drug flux through the stratum corneum. One such enhancement for transdermal drug delivery is referred to as "electrotransport." This mechanism uses an electrical potential, which results in the application of electric current to aid in the transport of the agent through a body surface, such as skin. Other active transport systems use ultrasound (phonophoresis) and heat as the external energy source.

There also have been many attempts to mechanically penetrate or disrupt the outermost skin layers thereby creating pathways into the skin in order to enhance the amount of agent being transdermally delivered. Early vaccination devices known as scarifiers generally had a plurality of tines or needles which are applied to the skin to scratch or make small cuts in the area of application. The vaccine was applied either topically on the skin, such as U.S. Pat. No. 5,487,726 issued to Rabenau or as a wetted liquid applied to the scarifier tines such as U.S. Pat. No. 4,453,926, issued to Galy or U.S. Pat. No. 4,109,655 issued to Chacornac, or U.S. Pat. No. 3,136,314 issued to Kravitz. Scarifiers have been suggested for intradermal vaccine delivery in part because only very small amounts of the vaccine need to be delivered into the skin to be effective in immunizing the patient. Further, the amount of vaccine delivered is not particularly critical since an excess amount achieves satisfactory immunization as well as a minimum amount. However a serious disadvantage in using a scarifier to deliver a drug is the difficulty in determining the transdermal drug flux and the resulting dosage delivered. Also due to the elastic, deforming and resilient nature of skin to deflect and resist puncturing, the tiny piercing elements often do not uniformly penetrate the skin and/or are wiped free of a liquid coating of an agent upon skin penetration. Additionally, due to the self healing process of the skin, the punctures or slits made in the skin tended to close up after removal of the piercing elements from the stratum corneum. Thus, the elastic nature of the skin acts to remove the active agent coating which has been applied to the tiny piercing elements upon penetration of these elements into the skin. Furthermore the tiny slits formed by the piercing elements heal quickly after removal of the device, thus limiting the passage of agent through the passageways created by the piercing elements and in turn limiting the transdermal flux of such devices.

Other devices which use tiny skin piercing elements to enhance transdermal drug delivery are disclosed in European Patent EP 0407063A1, U.S. Pat. No. 5,879,326 issued to Godshall, et al., U.S. Pat. No. 3,814,097 issued to Ganderton, et al., U.S. Pat. No. 5,279,544 issued to Gross, et al., U.S. Pat. No. 5,250,023 issued to Lee, et al., U.S. Pat. No. 3,964,482 issued to Gerstel, et al., Reissue 25,637 issued to Kravitz, et al., and PCT Publication Nos. WO 96/37155, WO 96/37256, WO 96/17648, WO 97/03718, WO 98/11937, WO 98/00193, WO 97/48440, WO 97/48441, WO 97/48442, WO 98/00193, WO 99/64580, WO 98/28037, WO 98/29298, and WO 98/29365; all incorporated by reference in their entirety. These devices use piercing elements of various shapes and sizes to pierce the outermost layer (i.e., the stratum corneum) of the skin. The piercing elements disclosed in these references generally extend perpendicularly from a thin, flat member, such as a pad or sheet. The piercing elements in some of these devices are extremely small, some having dimensions (i.e., a microblade length and width) of only about 25-400 μm and a microblade thickness of only about 5-50 μm. These tiny piercing/cutting elements make correspondingly small microslits/microcuts in the stratum corneum for enhanced transdermal agent delivery therethrough.

Generally, these systems include a reservoir for holding the drug and also a delivery system to transfer the drug from the reservoir through the stratum corneum, such as by hollow tines of the device itself. Another alternative is to provide a coating containing the active agent on the microprojections themselves. Such an approach has been disclosed in published U.S. patent application Ser. Nos. 2002/0132054, 2002/0193729, 2002/0177839, and 2002/0128599, all which are incorporated herein by reference.

Using a microprojection device to transdermally deliver an agent coated on the microprojections confers a number of benefits. However, some of the formulations used for coating the microprojections do not achieve a coating that is readily solubilized upon piercing the skin.

Accordingly, it is an object of the invention to provide a coating that has improved solubility.

It is another object of the invention to provide a coating that stabilizes the pH of the coating and can increase the amount of uncharged biologically active agent, which is less soluble in physiological fluids.

SUMMARY OF THE INVENTION

In accordance with the above objects and those that will be mentioned and will become apparent below, the device and method for transdermally delivering a biologically active agent in accordance with this invention generally comprises a delivery system having a microprojection member (or system) that includes at least one microprojection (or array thereof) that are adapted to pierce through the stratum corneum into the underlying epidermis layer, or epidermis and dermis layers. In one embodiment, the microprojection includes a biocompatible coating having at least one biologically active agent disposed therein.

As such, one embodiment of the invention is a composition for coating a transdermal delivery device having stratum corneum-piercing microprojections comprising a formulation of a biologically active agent and a non-volatile counterion, wherein said formulation has increased pH stability and solubility when dried.

Suitable biologically active agents include therapeutic agents in all the major therapeutic areas including, but not limited to: anti-infectives, such as antibiotics and antiviral agents; analgesics, including fentanyl, sufentanil, remifentanil, buprenorphine and analgesic combinations; anesthetics; anorexics; antiarthritics; antiasthmatic agents, such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives, such as atenolol; ACE inhibitors, such as ranitidine; diuretics; vasodilators, including general, coronary, peripheral, and cerebral; central nervous system stimulants; cough and cold preparations; decongestants; diagnostics; hormones, such as parathyroid hormone; hypnotics; immunosuppressants; muscle relaxants; parasympatholytics; parasympathomimetrics; prostaglandins; proteins; peptides; psychostimulants; sedatives; and tranquilizers. Other suitable agents include vasoconstrictors, anti-healing agents and pathway patency modulators.

Further specific examples of agents include, without limitation, growth hormone release hormone (GHRH), growth hormone release factor (GHRF), insulin, insultropin, calcitonin, octreotide, endorphin, thyroliberin (TRH), NT-36 (chemical name: N-[[(s)-4-oxo-2-azetidinyl]carbonyl]-L-histidyl-L-prolinamide), liprecin, pituitary hormones (e.g., human growth hormone (HGH), menotropin (hMG), desmopressin acetate, etc), follicle luteoids, alpha natriuretic factor (aANF), growth factors such as growth factor releasing factor (GFRF), beta-melanocyte-stimulating hormone (bMSH), growth hormone (GH), somatostatin, bradykinin, somatotropin, platelet-derived growth factor releasing factor, asparaginase, bleomycin sulfate, chymopapain, cholecystokinin, chorionic gonadotropin, erythropoietin, epoprostenol (platelet aggregation inhibitor), glucagon, human chorionic gonadotropin (HCG), hirulog, hyaluronidase, interferon alpha, interferon beta, interferon gamma, interleukins, interleukin-10 (IL-10), erythropoietin (EPO), granulocyte macrophage colony stimulating factor (GM-CSF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, menotropins (urofollitropin (follicle stimulating hormone (FSH) and leutinizing hormone (LH))), oxytocin, streptokinase, tissue plasminogen activator, urokinase, vasopressin, deamino [Val4, D-Arg8] arginine vasopressin, desmopressin, corticotropin (adrenocorticotropic hormone (ACTH)), ACTH analogs such as ACTH (1-24), atrial natriuretic peptide (ANP), ANP clearance inhibitors, angiotensin II antagonists, antidiuretic hormone agonists, bradykinin antagonists, ceredase, corticostatin analogs (CSI's), calcitonin gene related peptide (CGRP), enkephalins, FAB fragments, IgE peptide suppressors, insulin-like growth factor-1 (IGF-1), neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin alpha-1, thrombolytics, tumor necrosis factor (TNF), vasopressin antagonists analogs, alpha-1 antitrypsin (recombinant), and transforming growth factor-beta (TGF-beta).

The biologically active agent can also comprise a vaccine, including viruses and bacteria, protein-based vaccines, polysaccharide-based vaccine, nucleic acid-based vaccines, and other antigenic agents. Suitable antigenic agents include, without limitation, antigens in the form of proteins, polysaccharide conjugates, oligosaccharides, and lipoproteins. These subunit vaccines in include *Bordetella pertussis* (recombinant PT accince-acellular), *Clostridium tetani* (purified, recombinant), *Corynebacterium diptheriae* (purified, recombinant), *Cytomegalovirus* (glycoprotein subunit), Group A streptococcus (glycoprotein subunit, glycoconjugate Group A polysaccharide with tetanus toxoid, M protein/peptides linke to toxing subunit carriers, M protein, multivalent type-specific epitopes, cysteine protease, C5a peptidase), Hepatitis B virus (recombinant Pre S 1, Pre-S2, S, recombinant core protein), Hepatitis C virus (recombinant-expressed surface proteins and epitopes), Human papillomavirus (Capsid protein, TA-GN recombinant protein L2 and E7 [from HPV-6], MEDI-501 recombinant VLP L1 from HPV-11, Quadrivalent recombinant BLP L1 [from HPV-6], HPV-11, HPV-16, and HPV-18, LAMP-E7 [from HPV-16]), *Legionella pneumophila* (purified bacterial survace protein), *Neisseria meningitides* (glycoconjugate with tetanus toxoid), *Pseudomonas aeruginosa* (synthetic peptides), Rubella virus (synthetic peptide), *Streptococcus pneumoniae* (glyconconjugate [1, 4, 5, 6B, 9N, 14, 18C, 19V, 23F] conjugated to meningococcal B OMP, glycoconjugate [4, 6B, 9V, 14, 18C, 19F, 23F] conjugated to CRM197, glycoconjugate [1, 4, 5, 6B, 9V, 14, 18C, 19F, 23F] conjugated to CRM1970, *Treponema pallidum* (surface lipoproteins), Varicella zoster virus (subunit, glycoproteins), and *Vibrio cholerae* (conjugate lipopolysaccharide).

Whole virus or bacteria include, without limitation, weakened or killed viruses, such as cytomegalo virus, hepatitis B virus, hepatitis C virus, human papillomavirus, rubella virus, and varicella zoster, weakened or killed bacteria, such as *bordetella pertussis, clostridium tetani, corynebacterium diptheriae*, group A streptococcus, *legionella pneumophila, neisseria meningitdis, pseudomonas aeruginosa, streptococcus pneumoniae, treponema pallidum*, and *vibrio cholerae*, and mixtures thereof.

Additional commercially available vaccines, which contain antigenic agents, include, without limitation, flu vaccines, lyme disease vaccine, rabies vaccine, measles vaccine, mumps vaccine, chicken pox vaccine, small pox vaccine, hepatitus vaccine, pertussis vaccine, and diptheria vaccine.

Vaccines comprising nucleic acids include, without limitation, single-stranded and double-stranded nucleic acids, such as, for example, supercoiled plasmid DNA; linear plasmid DNA; cosmids; bacterial artificial chromosomes (BACs); yeast artificial chromosomes (YACs); mammalian artificial chromosomes; and RNA molecules, such as, for example, mRNA. The size of the nucleic acid can be up to thousands of kilobases. In addition, in certain embodiments of the invention, the nucleic acid can be coupled with a proteinaceous agent or can include one or more chemical modifications, such as, for example, phosphorothioate moieties. The encoding sequence of the nucleic acid comprises the sequence of the antigen against which the immune response is desired. In addition, in the case of DNA, promoter and polyadenylation sequences are also incorporated in the vaccine construct. The antigen that can be encoded include all antigenic components of infectious diseases, pathogens, as well as cancer antigens. The nucleic acids thus find application, for example, in the fields of infectious diseases, cancers, allergies, autoimmune, and inflammatory diseases.

Suitable immune response augmenting adjuvants which, together with the vaccine antigen, can comprise the vaccine include aluminum phosphate gel; aluminum hydroxide; algal glucan: b-glucan; cholera toxin B subunit; CRL1005: ABA block polymer with mean values of x=8 and y=205; gamma inulin: linear (unbranched) β-D(2->1) polyfructofuranoxyl-a-D-glucose; Gerbu adjuvant: N-acetylglucosamine-(b 1-4)-N-acetylmuramyl-L-alanyl-D-glutamine (GMDP), dimethyl dioctadecylammonium chloride (DDA), zinc L-proline salt complex (Zn-Pro-8); Imiquimod (1-(2-methypropyl)-1H-imidazo[4,5-c]quinolin-4-amine; ImmTherÔ: N-acetylglucoaminyl-N-acetylmuramyl-L-Ala-D-isoGlu-L-Ala-glycerol dipalmitate; MTP-PE liposomes: C59H108N6O19PNa-3H20 (MTP); Murametide: Nac-Mur-L-Ala-D-Gln-OCH3; Pleuran: b-glucan; QS-21; S-28463: 4-amino-a, a-dimethyl-1H-imidazo[4,5-c]quinoline-1-ethanol; sclavo peptide: VQGEESNDK.HCl (IL-1b 163-171 peptide); and threonyl-MDP (TermurtideÔ): N-acetyl muramyl-L-threonyl-D-isoglutamine, and interleukine 18, IL-2 IL-12, IL-15, Adjuvants also include DNA oligonucleotides, such as, for example, CpG containing oligonucleotides. In addition, nucleic acid sequences encoding for immuno-regulatory lymphokines such as IL-18, IL-2 IL-12, IL-15, IL-4, IL10, gamma interferon, and NF kappa B regulatory signaling proteins can be used.

Generally, in the noted embodiments of the invention, the amount of counterion should neutralize the charge of the biologically active agent. In such embodiments, the counterion or the mixture of counterion is present in amounts necessary to neutralize the charge present on the agent at the pH of the formulation. Excess of counterion (as the free acid or as a salt) can be added to the peptide in order to control pH and to provide adequate buffering capacity.

In another preferred embodiment the counterion is a strong acid. Strong acids can be defined as presenting at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid.

Another preferred embodiment is directed to a mixture of counterions wherein at least one of the counterion is a strong acid and at least one of the counterion is a low volatility weak acid.

Another preferred embodiment is directed to a mixture of counterions wherein at least one of the counterion is a strong acid and at least one of the counterion is a weak acid with high volatility. Volatile weak acid counterions present at least one pKa higher than about 2 and a melting point lower than about 50° C. or a boiling point lower than about 170° C. at $P_{atm}$. Examples of such acids include acetic acid, propionic acid, pentanoic acid and the like.

The acidic counterion is present in amounts necessary to neutralize the positive charge present on the drug at the pH of the formulation. Excess of counterion (as the free acid or as a salt) can be added to the drug in order to control pH and to provide adequate buffering capacity.

In one embodiment of the invention, the coating formulations include at least one antioxidant, which can be sequestering agents such sodium citrate, citric acid, EDTA (ethylene-dinitrilo-tetraacetic acid) or free radical scavengers such as ascorbic acid, methionine, sodium ascorbate, and the like.

In one embodiment of the invention, the coating formulation includes at least one surfactant, which can be zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates such as TWEEN® 20 (polyoxyethylene-20-sorbitan monolaurate) and TWEEN® 80 (polyoxyethylene-80-sorbitan monolaurate) TWEEN 80, other sorbitan derivatives, such as sorbitan laurate, and alkoxylated alcohols, such as laureth-4.

In a further embodiment of the invention, the coating formulation includes at least one polymeric material or polymer that has amphiphilic properties, which can comprise, without limitation, cellulose derivatives, such as hydroxyethylcellulose (HEC), hydroxypropylmethylcell-ulose (HPMC), hydroxypropycellulose (HPC), methylcellulose (MC), hydroxyethylmethylcellulose (HEMC), or ethylhydroxy-ethylcellulose (EHEC), as well as PLURONIC® type copolymers.

In another embodiment, the coating formulation includes a hydrophilic polymer selected from the following group: hydroxyethyl starch, dextran, poly(vinyl alcohol), poly(ethylene oxide), poly(2-hydroxyethylmethacrylate), poly(n-vinyl pyrolidone), polyethylene glycol and mixtures thereof, and like polymers.

In another embodiment of the invention, the coating formulation includes a biocompatible carrier, which can comprise, without limitation, human albumin, bioengineered human albumin, polyglutamic acid, polyaspartic acid, polyhistidine, pentosan polysulfate, polyamino acids, sucrose, trehalose, melezitose, raffinose and stachyose.

In another embodiment, the coating formulation includes a stabilizing agent, which can comprise, without limitation, a non-reducing sugar, a polysaccharide or a reducing sugar. Suitable non-reducing sugars for use in the methods and compositions of the invention include, for example, sucrose, trehalose, stachyose, or raffinose. Suitable polysaccharides for use in the methods and compositions of the invention include, for example, dextran, soluble starch, dextrin, and insulin. Suitable reducing sugars for use in the methods and compositions of the invention include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

In another embodiment, the coating formulation includes a vasoconstrictor, which can comprise, without limitation, amidephrine, cafaminol, cyclopentamine, deoxyepinephrine, epinephrine, felypressin, indanazoline, metizoline, midodrine, naphazoline, nordefrin, octodrine, omipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and the mixtures thereof. The most preferred vasoconstrictors include epinephrine, naphazoline, tetrahydrozoline indanazoline, metizoline, tramazoline, tymazoline, oxymetazoline and xylometazoline.

In another embodiment of the invention, the coating formulation includes at least one "pathway patency modulator", which can comprise, without limitation, osmotic agents (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

In yet another embodiment of the invention, the coating formulation includes a solubilizing/complexing agent, which can comprise Alpha-Cyclodextrin, Beta-Cyclodextrin, Gamma-Cyclodextrin, glucosyl-alpha-Cyclodextrin, maltosyl-alpha-Cyclodextrin, glucosyl-beta-Cyclodextrin, maltosyl-beta-Cyclodextrin, hydroxypropyl beta-cyclodextrin, 2-hydroxypropyl-beta-Cyclodextrin, 2-hydroxypropyl-gamma-Cyclodextrin, hydroxyethyl-beta-Cyclodextrin, methyl-beta-Cyclodextrin, sulfobutylether-alpha-cyclodextrin, sulfobutylether-beta-cyclodextrin, and sulfobutylether-gamma-cyclodextrin. Most preferred solubilizing/complexing agents are beta-cyclodextrin, hydroxypropyl beta-cyclodextrin, 2-hydroxypropyl-beta-Cyclodextrin and sulfobutylether7 beta-cyclodextrin.

In another embodiment of the invention, the coating formulation includes at least one non-aqueous solvent, such as ethanol, isopropanol, methanol, propanol, butanol, propylene glycol, dimethysulfoxide, glycerin, N,N-dimethylformamide and polyethylene glycol 400.

Preferably, the coating formulations have a viscosity less than approximately 500 centipoise and greater than 3 centipoise.

In one embodiment of the invention, the thickness of the biocompatible coating is less than 25 microns, more preferably, less than 10 microns.

The invention also comprises transdermal delivery devices having at least one microprojection configured to pierce the stratum corneum coated with the noted formulations.

In one embodiment of the invention, the device has a microprojection density of at least approximately 10 microprojections/$cm^2$, more preferably, in the range of at least approximately 200-2000 microprojections/$cm^2$.

In one embodiment, the microprojection is constructed out of stainless steel, titanium, nickel titanium alloys, or similar biocompatible materials.

In another embodiment, the microprojection is constructed out of a non-conductive material, such as a polymer. Alternatively, the microprojection can be coated with a non-conductive material, such as Parylene®, or a hydrophobic material, such as Teflon®, silicon or other low energy material.

Generally, the methods of the invention comprise applying a coating of a biologically active agent to a transdermal delivery device, wherein the transdermal delivery device comprises a plurality of stratum corneum-piercing microprojections, comprising the steps of providing a formulation of the biologically active agent, stabilizing the formulation by adding a non-volatile counterion, and applying said formulation to the microprojections. Preferably, the counterion is added in an amount to neutralize the charge on the biologically active agent. The charge of the agent can be determined using the algorithms of the invention.

BRIEF DESCRIPTION OF THE DRAWINGS

The invention will now be described in greater detail with reference to the preferred embodiments illustrated in the accompanying drawings and figures wherein:

FIG. 3 is a graph showing the charge profile of fentanyl as a function of pH.

FIG. 4 is a graph showing the mole ratios of the neutral (Fentanyl base) and charged (Fentanyl+1) fentanyl species as a function of pH;

DETAILED DESCRIPTION OF THE INVENTION

Definitions

Figure 1:
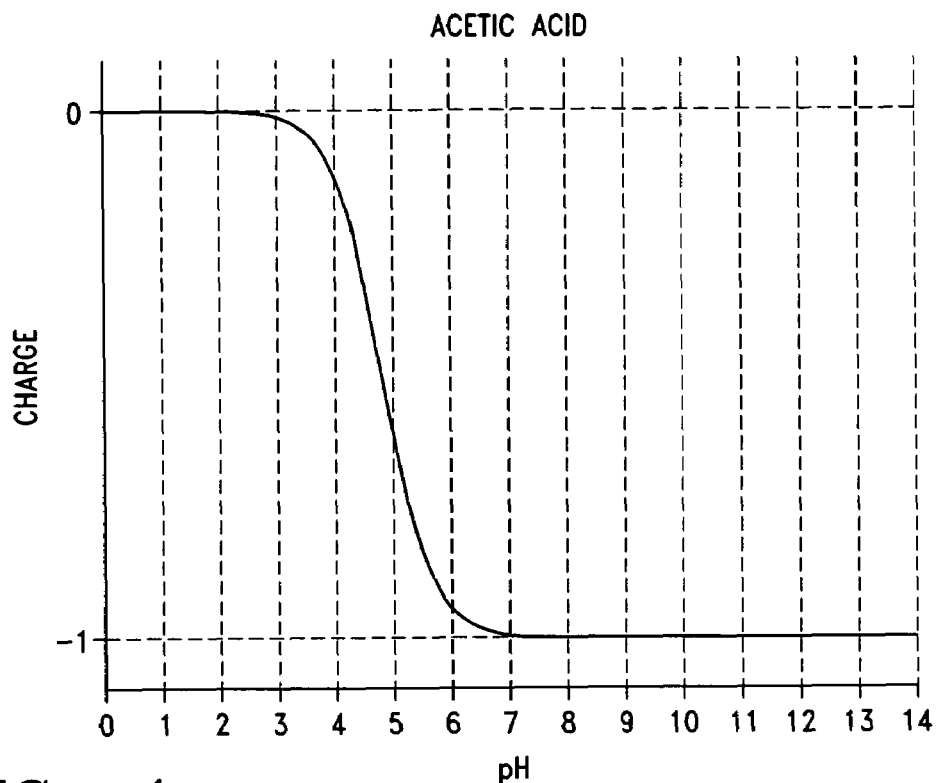
FIG. 1 is a graph showing the charge profile of acetic acid (pKa 4.75) as a function of pH.

Unless stated otherwise the following terms used herein have the following meanings.

The term "transdermal" means the delivery of an agent into and/or through the skin for local or systemic therapy.

The term "transdermal flux" means the rate of transdermal delivery.

The term "co-delivering" as used herein, means that a supplemental agent(s) is administered transdermally either before the agent is delivered, before and during transdermal flux of the agent, during transdermal flux of the agent, during and after transdermal flux of the agent, and/or after transdermal flux of the agent. Additionally, two or more agents may be coated onto the microprojections resulting in co-delivery of the agents.

The term "biologically active agent" or "active agent" as used herein, refers to a composition of matter or mixture containing a drug which is pharmacologically effective when administered in a therapeutically effective amount.

Such agents include therapeutic agents in all the major therapeutic areas including, but not limited to: anti-infectives such as antibiotics and antiviral agents; analgesics, including fentanyl, sufentanil, remifentanil, buprenorphine and analgesic combinations; anesthetics; anorexics; antiarthritics; antiasthmatic agents such as terbutaline; anticonvulsants; antidepressants; antidiabetic agents; antidiarrheals; antihistamines; anti-inflammatory agents; antimigraine preparations; antimotion sickness preparations such as scopolamine and ondansetron; antinauseants; antineoplastics; antiparkinsonism drugs; antipruritics; antipsychotics; antipyretics; antispasmodics, including gastrointestinal and urinary; anticholinergics; sympathomimetrics; xanthine derivatives; cardiovascular preparations, including calcium channel blockers such as nifedipine; beta blockers; beta-agonists such as dobutamine and ritodrine; antiarrythmics; antihypertensives such as atenolol; ACE inhibitors such as ranitidine; diuretics; vasodilators, including general, coronary, peripheral, and cerebral; central nervous system stimulants; cough and cold preparations; decongestants; diagnostics; hormones such as parathyroid hormone; hypnotics; immunosuppressants; muscle relaxants; parasympatholytics; parasympathomimetrics; prostaglandins; proteins; peptides; psychostimulants; sedatives; and tranquilizers. Other suitable agents include vasoconstrictors, anti-healing agents and pathway patency modulators.

Further specific examples of agents include, without limitation, growth hormone release hormone (GHRH), growth hormone release factor (GHRF), insulin, insultropin, calcitonin, octreotide, endorphin, thyroliberin (TRH), NT-36 (chemical name: N-[[(s)-4-oxo-2-azetidinyl]carbonyl]-L-histidyl-L-prolinamide), liprecin, pituitary hormones (e.g., human growth hormone (HGH), menotropin (hMG), desmopressin acetate, etc), follicle luteoids, alpha natriuretic factor (aANF), growth factors such as growth factor releasing factor (GFRF), beta-melanocyte-stimulating hormone (bMSH), growth hormone (GH), somatostatin, bradykinin, somatotropin, platelet-derived growth factor releasing factor, asparaginase, bleomycin sulfate, chymopapain, cholecystokinin, chorionic gonadotropin, erythropoietin, epoprostenol (platelet aggregation inhibitor), glucagon, human chorionic gonadotropin (HCG), hirulog, hyaluronidase, interferon alpha, interferon beta, interferon gamma, interleukins, interleukin-10 (IL-10), erythropoietin (EPO), granulocyte macrophage colony stimulating factor (GM-CSF), granulocyte colony stimulating factor (G-CSF), glucagon, leutinizing hormone releasing hormone (LHRH), LHRH analogs (such as goserelin, leuprolide, buserelin, triptorelin, gonadorelin, and napfarelin, menotropins (urofollitropin (follicle stimulating hormone (FSH) and leutinizing hormone (LH))), oxytocin, streptokinase, tissue plasminogen activator, urokinase, vasopressin, deamino [Val4, D-Arg8] arginine vasopressin, desmopressin, corticotropin (adrenocorticotropic hormone (ACTH)), ACTH analogs such as ACTH (1-24), atrial natriuretic peptide (ANP), ANP clearance inhibitors, angiotensin II antagonists, antidiuretic hormone agonists, bradykinin antagonists, ceredase, corticostatin analogs (CSI's), calcitonin gene related peptide (CGRP), enkephalins, FAB fragments, IgE peptide suppressors, insulin-like growth factor-1 (IGF-1), neurotrophic factors, colony stimulating factors, parathyroid hormone and agonists, parathyroid hormone antagonists, parathyroid hormone (PTH), PTH analogs such as PTH (1-34), prostaglandin antagonists, pentigetide, protein C, protein S, renin inhibitors, thymosin alpha-1, thrombolytics, tumor necrosis factor (TNF), vasopressin antagonists analogs, alpha-1 antitrypsin (recombinant), and transforming growth factor-beta (TGF-beta).

The term "biologically active agent" or "active agent" as used herein also refers to a composition of matter or mixture containing a vaccine or other immunologically active agent or an agent which is capable of triggering the production of an immunologically active agent, and which is directly or indirectly immunologically effective when administered in a immunologically effective amount.

Suitable vaccines include viruses and bacteria, protein-based vaccines, polysaccharide-based vaccine, nucleic acid-based vaccines, and other antigenic agents. Suitable antigenic agents include, without limitation, antigens in the form of proteins, polysaccharide conjugates, oligosaccharides, and lipoproteins. Subunit vaccines include *Bordetella pertussis* (recombinant pertussis toxin vaccine—acellular), *Clostridium tetani* (purified, recombinant), *Corynebacterium diptheriae* (purified, recombinant), *Cytomegalovirus* (glycoprotein subunit), Group A streptococcus (glycoprotein subunit, glycoconjugate Group A polysaccharide with tetanus toxoid, M protein/peptides linked to toxin subunit carriers, M protein, multivalent type-specific epitopes, cysteine protease, C5a peptidase), Hepatitis B virus (recombinant Pre S1, Pre-S2, S, recombinant core protein), Hepatitis C virus (recombinant-expressed surface proteins and epitopes), Human papillomavirus (Capsid protein, TA-GN recombinant protein L2 and E7 [from HPV-6], MEDI-501 recombinant VLP L1 from HPV-11, Quadrivalent recombinant BLP L1 [from HPV-6], HPV-11, HPV-16, and HPV-18, LAMP-E7 [from HPV-16]), *Legionella pneumophila* (purified bacterial surface protein), *Neisseria meningitides* (glycoconjugate with tetanus toxoid), *Pseudomonas aeruginosa* (synthetic peptides), Rubella virus (synthetic peptide), *Streptococcus pneumoniae* (glyconconjugate [1, 4, 5, 6B, 9N, 14, 18C, 19V, 23F] conjugated to meningococcal B OMP, glycoconjugate [4, 6B, 9V, 14, 18C, 19F, 23F] conjugated to CRM197, glycoconjugate [1, 4, 5, 6B, 9V, 14, 18C, 19F, 23F] conjugated to CRM1970, *Treponema pallidum* (surface lipoproteins), Varicella zoster virus (subunit, glycoproteins), and *Vibrio cholerae* (conjugate lipopolysaccharide).

Whole virus or bacteria include, without limitation, weakened or killed viruses, such as cytomegalo virus, hepatitis B virus, hepatitis C virus, human papillomavirus, rubella virus, and varicella zoster, weakened or killed bacteria, such as *bordetella pertussis, clostridium tetani, corynebacterium diptheriae*, group A streptococcus, *legionella pneumophila, neisseria meningitdis, pseudomonas aeruginosa, streptococcus pneumoniae, treponema pallidum*, and *vibrio cholerae*, and mixtures thereof.

Additional commercially available vaccines, which contain antigenic agents, include, without limitation, flu vaccines, lyme disease vaccine, rabies vaccine, measles vaccine, mumps vaccine, chicken pox vaccine, small pox vaccine, hepatitus vaccine, pertussis vaccine, and diptheria vaccine.

Vaccines comprising nucleic acids include, without limitation, single-stranded and double-stranded nucleic acids, such as, for example, supercoiled plasmid DNA; linear plasmid DNA; cosmids; bacterial artificial chromosomes (BACs); yeast artificial chromosomes (YACs); mammalian artificial chromosomes; and RNA molecules, such as, for example, mRNA. The size of the nucleic acid can be up to thousands of kilobases. In addition, in certain embodiments of the invention, the nucleic acid can be coupled with a proteinaceous agent or can include one or more chemical modifications, such as, for example, phosphorothioate moieties. The encoding sequence of the nucleic acid comprises the sequence of the antigen against which the immune response is desired. In addition, in the case of DNA, promoter and polyadenylation sequences are also incorporated in the vaccine construct. The antigen that can be encoded include all antigenic components of infectious diseases, pathogens, as well as cancer antigens. The nucleic acids thus find application, for example, in the fields of infectious diseases, cancers, allergies, autoimmune, and inflammatory diseases.

Suitable immune response augmenting adjuvants which, together with the vaccine antigen, can comprise the vaccine include aluminum phosphate gel; aluminum hydroxide; algal glucan: b-glucan; cholera toxin B subunit; CRL1005: ABA block polymer with mean values of x=8 and y=205; gamma inulin: linear (unbranched) β-D(2->1) polyfructofuranoxyl-a-D-glucose; Gerbu adjuvant: N-acetylglucosamine-(b 1-4)-N-acetylmuramyl-L-alanyl-D-glutamine (GMDP), dimethyl dioctadecylammonium chloride (DDA), zinc L-proline salt complex (Zn-Pro-8); Imiquimod (1-(2-methypropyl)-1H-imidazo[4,5-c]quinolin-4-amine; ImmTherÒ: N-acetylglucoaminyl-N-acetylmuramyl-L-Ala-D-isoGlu-L-Ala-glycerol dipalmitate; MTP-PE liposomes: C59H108N6O19PNa-3H20 (MTP); Murametide: Nac-Mur-L-Ala-D-Gln-OCH3; Pleuran: b-glucan; QS-21; S-28463: 4-amino-a, a-dimethyl-1H-imidazo[4,5-c]quinoline-1-ethanol; sclavo peptide: VQGEESNDK.HCl (IL-1b 163-171 peptide); and threonyl-MDP (TermurtideÔ): N-acetyl muramyl-L-threonyl-D-isoglutamine, and interleukine 18, IL-2 IL-12, IL-15, Adjuvants also include DNA oligonucleotides, such as, for example, CpG containing oligonucleotides. In addition, nucleic acid sequences encoding for immuno-regulatory lymphokines such as IL-18, IL-2 IL-12, IL-15, IL-4, IL10, gamma interferon, and NF kappa B regulatory signaling proteins can be used.

It is to be understood that more than one agent may be incorporated into the agent formulation in the method of this invention, and that the use of the term "active agent" in no way excludes the use of two or more such agents or drugs. The agents can be in various forms, such as free bases, acids, charged or uncharged molecules, components of molecular complexes or nonirritating, pharmacologically acceptable salts. Also, simple derivatives of the agents (such as ethers, esters, amides, etc) which are easily hydrolyzed at body pH, enzymes, etc., can be employed.

The term "biologically effective amount" or "biologically effective rate" shall be used when the biologically active agent is a pharmaceutically active agent and refers to the amount or rate of the pharmacologically active agent needed to effect the desired therapeutic, often beneficial, result. The amount of agent employed in the coatings will be that amount necessary to deliver a therapeutically effective amount of the agent to achieve the desired therapeutic result. In practice, this will vary widely depending upon the particular pharmacologically active agent being delivered, the site of delivery, the severity of the condition being treated, the desired therapeutic effect and the dissolution and release kinetics for delivery of the agent from the coating into skin tissues. It is not practical to define a precise range for the therapeutically effective amount of the pharmacologically active agent incorporated into the microprojections and delivered transdermally according to the methods described herein.

The term "biologically effective amount" or "biologically effective rate" may also be used when the biologically active agent is an immunologically active agent and refers to the amount or rate of the immunologically active agent needed to stimulate or initiate the desired immunologic, often beneficial result. The amount of the immunologically active agent employed in the coatings will be that amount necessary to deliver an amount of the agent needed to achieve the desired immunological result. In practice, this will vary widely depending upon the particular immunologically active agent being delivered, the site of delivery, and the dissolution and release kinetics for delivery of the agent from the coating into skin tissues.

The term "microprojections" refers to piercing elements which are adapted to pierce or cut through the stratum corneum into the underlying epidermis layer, or epidermis and dermis layers, of the skin of a living animal, particularly a human. The piercing elements should not pierce the skin to a depth which causes bleeding. Typically the piercing elements have a blade length of less than 500 μm, and preferably less than 250 μm. The microprojections typically have a width of about 10 to 200 μm and thickness of about 5 to 50 μm. The microprojections may be formed in different shapes, such as needles, hollow needles, blades, pins, punches, and combinations thereof.

Figure 11:
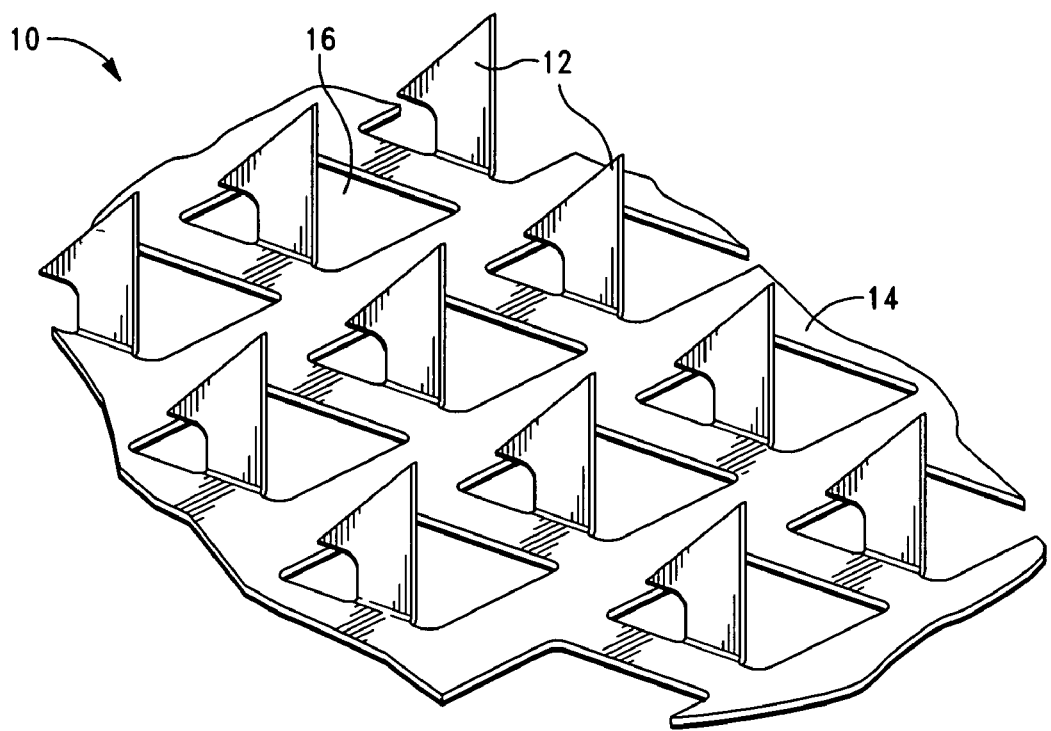
FIG. 11 is a perspective view of a microprojection array that would be used in conjunction with the present invention.
Figure 12:
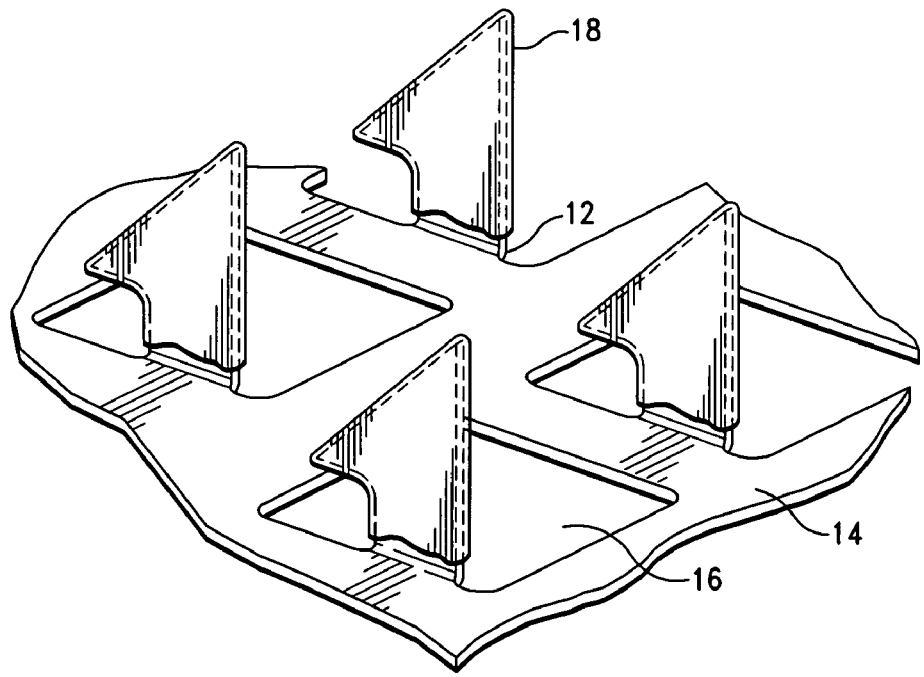
FIG. 12 is a perspective view of a microprojection array showing several microprojections that have been coated.

The term "microprojection array" as used herein, refers to a plurality of microprojections arranged in an array for piercing the stratum corneum. The microprojection array may be formed by etching or punching a plurality of microprojections from a thin sheet and folding or bending the microprojections out of the plane of the sheet to form a configuration such as that shown in FIG. 11. The microprojection array may also be formed in other known manners, such as by forming one or more strips having microprojections along an edge of each of the strip(s) as disclosed in Zuck, U.S. Pat. No. 6,050,988. The microprojection array may include hollow needles which hold a dry pharmacologically active agent.

The term "polyelectrolyte" as used herein, means formulations of biologically active agents having ionic species. A polyelectrolyte is a macromolecular substance which, on dissolving in water or another ionizing solvent, dissociates to give multiply charged anions or cations. For example, agents comprising polypeptides frequently have complex ionic characters resulting from multiple amino acid residues having acidic and basic functionalities.

Volatile counterions are defined as weak acids presenting at least one pKa higher than about 2 and a melting point lower than about 50° C. or a boiling point lower than about 170° C. at $P_{atm}$. Examples of such acids include acetic acid, propionic acid, pentanoic acid and the like. Volatile counterions are also defined as weak bases presenting at least one pKa lower than about 12 and a melting point lower than about 50° C. or a boiling point lower than about 170° C. at $P_{atm}$. Examples of such bases include ammonia and morpholine.

Non-volatile counterions are defined as weak acids presenting at least one acidic pKa and a melting point higher than about 50° C. or a boiling point higher than about 170° C. at $P_{atm}$. Examples of such acids include citric acid, succinic acid, glycolic acid, gluconic acid, glucuronic acid, lactic acid, malic acid, pyruvic acid, tartaric acid, tartronic acid, and fumaric acid. Non-volatile counterions are also defined as acidic zwitterions presenting at least two acidic pKa, and at least one basic pKa, so that there is at least one extra acidic group as compared to the number of basic groups. Examples of such compounds include glutamic acid and aspartic acid.

Non-volatile counterions are also defined as weak bases presenting at least one basic pKa and a melting point higher than about 50° C. or a boiling point higher than about 170° C. at $P_{atm}$. Examples of such bases include monoethanolomine, diethanolamine, triethanolamine, tromethamine, methylglucamine, glucosamine. Non-volatile counterions are also defined as basic zwitterions presenting at least one acidic pKa, and at least two basic pKa's, wherein the number of basic pKa's is greater than the number of acidic pka's. Examples of such compounds include histidine, lysine, and arginine.

Non-volatile counterions are also defined as strong acids presenting at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid. Non-volatile counterions are further defined as strong bases presenting at least one pKa higher than about 12. Examples of such bases include sodium hydroxide, potassium hydroxide, calcium hydroxide, and magnesium hydroxide.

When referring to the volatility of a counterion, reference will always be made to the volatility of the non-ionized form of the counterion (e.g. acetic acid versus acetate).

Some drugs behave like strong bases or strong acids (for example quaternary ammonium salts such as clidinium bromide or glycopyrrolate, sulfate derivatives such as pentosan polysulfate, some phosphoric derivatives such as nucleic acids) and are totally ionized in a wide range of pH (i.e., 4-10) that is commonly used to manufacture pharmaceutical formulations. Other compounds, such as neutral polysaccharides (ie., insulin and dextrans), do not present acidic or basic functions. For these classes of compounds, solubility in water is not significantly affected by pH, and the invention does not apply.

Conversely, many drugs behave as weak acids or weak bases. Their neutral forms usually present low water solubility. For example the neutral form of many small molecular compounds such as fentanyl or peptides such as hPTH(1-34) are notoriously insoluble in water. These compounds exhibit maximum solubility in water when they are in an electrically charged state. Because of their weakly acidic or basic nature, the respective concentrations of the neutral and ionized forms and, hence, the solubility in water, is pH dependant. The invention applies to this class of drugs. As will be evident from the examples discussed below, combination of this type of drug with a non-volatile counterion in ratios sufficient to minimize the presence of the neutral form of the drug assures water solubility of the drug in the formulation, stability during storage in the solid state, and dissolution in the biological fluids at the time of administration.

References to the area of the sheet or member and reference to some property per area of the sheet or member are referring to the area bounded by the outer circumference or border of the sheet.

The term "pattern coating" refers to coating an agent onto selected areas of the microprojections. More than one agent may be pattern coated onto a single microprojection array. Pattern coatings can be applied to the microprojections using known micro-fluid dispensing techniques such as micropipeting and ink jet coating.

The drugs that will benefit from this invention contain at least one weak acidic and/or one weak basic function and are present as a neutral species in the pH range pH 4 to pH 10. The mole ratio between the uncharged species and the charged species should be at least 1 to 100 in this pH range.

The non-volatile counterion is present in an amount sufficient to reduce the mole ratio between the uncharged species and the charged species of the drug to less than about 1 to 100.

The present invention is based upon the discovery that coatings made from formulations that incorporate volatile counterions will lose the volatile counterions from the outer surface of the coating. This results in a shift in the pH of the coating and can increase the amount of uncharged biologically active agent, which is less soluble in physiological fluids.

The present invention provides a coating formulation containing a biologically active agent which when coated and dried upon one or more microprojections forms a coating which reduces the loss of counterions from the coating, stabilized the pH of the coating and enhances the solubilization of the coating upon insertion into the skin. The present invention further includes a device having a plurality of stratum corneum-piercing microprojections extending therefrom. The microprojections are adapted to pierce through the stratum corneum into the underlying epidermis layer, or epidermis and dermis layers, but do not penetrate so deep as to reach the capillary beds and cause significant bleeding. The microprojections have a dry coating thereon which contains the biologically active agent. The coating is formulated to reduce, minimize and/or eliminate loss of volatile counter ions from the coating which enhances solubilization of the coating upon piercing the skin. Upon piercing the stratum corneum layer of the skin, the agent-containing coating is dissolved by body fluid (intracellular fluids and extracellular fluids such as interstitial fluid) and released into the skin for local or systemic therapy.

The solid coating is obtained by drying a formulation on the microprojection, as described in U.S. patent application Publication No. 2002/0128599. The formulation is usually an aqueous formulation. During the drying process, all volatiles, including water are mostly removed (the final solid coating still contains up to about 10% water). If a volatile compound that is in equilibrium between its ionized and non-ionized forms is present in solution, only the non-ionized form disappears from the formulation at the time where the drying process takes place and the ionized form stays in solution and incorporated into the coating.

In a solid coating on a microprojection array, the drug is typically present in an amount of less than about 1 mg per unit dose. With the addition of excipients and counterions, the total mass of solid coating is less than 3 mg per unit dose. The array is usually present on an adhesive backing, which is attached to a disposable polymeric retainer ring. This assembly is packaged individually in a pouch or a polymeric housing.

In addition to the assembly, this package contains an atmosphere (usually inert) that represents a volume of at least 3 mL. This large volume (as compared to that of the coating) acts as a sink for any volatile component. For example, at 20° C., the amount of acetic acid present in a 3 mL atmosphere as a result of its vapor pressure would be about 0.15 mg. This amount is typically what would be present in the solid coating if acetic acid were used as a counterion. In addition, components of the assembly such as the adhesive are likely to act as additional sinks for volatile components. As a result, during long-term storage, it is likely that the concentration of any volatile component present in the coating would change dramatically.

The above conditions are atypical of traditional packaging of pharmaceutical compounds where large amounts of excipients are usually present. Even with very potent biotechnology compounds that are lyophilized for use as injectable, very large excess of buffers and excipients are present in the dry cake. Thus the effect of loss of volatile counterion-ions does not effect the solubilization of these traditional dosage forms.

In the case of a drug of interest bearing a positive charge at the desired pH, the counterion is an acid. In a preferred embodiment, the acidic counterion is a non-volatile weak acid. In another preferred embodiment, the counterion is a non-volatile strong acid.

Another preferred embodiment is directed to a mixture of counterions wherein at least one of the counterions is a strong acid and at least one of the counterion is a non-volatile weak acid.

Another preferred embodiment is directed to a mixture of counterions wherein at least one of the counterions is a non-volatile acid and at least one of the counterions is a weak acid with high volatility.

The acidic counterion is present in amounts necessary to neutralize the positive charge present on the drug at the pH of the formulation. Excess of counterion (as the free acid or as a salt) can be added to the drug in order to control pH and to provide adequate buffering capacity.

In the case of a drug of interest bearing a negative charge at the desired pH, the counterion is a base.

In a preferred embodiment, the basic counterion is a weak base with low volatility.

In another preferred, embodiment the counterion is a strong base.

Another preferred embodiment is directed to a mixture of counterions wherein at least one of the counterions is a strong base and at least one of the counterions is a weak base with low volatility.

Another preferred embodiment is directed to a mixture of counterions wherein at least one of the counterions is a non-volatile base and at least one of the counterions is a weak base with high volatility.

The basic counterion is present in amounts necessary to neutralize the negative charge present on the drug of interest at the pH of the formulation. Excess of counterion (as the free base or as a salt) can be added to the drug in order to control pH and to provide adequate buffering capacity.

The present invention relates to a pharmaceutical dosage form which is a solid coating applied to one or more microprojections on a microprojection array. The coating contains an ionized drug which has at least one weak and/or one basic functional group The kinetics of the agent-containing coating dissolution and release will depend on many factors including the nature of the drug, the coating process, the coating thickness and the coating composition (e.g., the presence of coating formulation additives). Depending on the release kinetics profile, it may be necessary to maintain the coated microprojections in piercing relation with the skin for extended periods of time (e.g., up to about 8 hours). This can be accomplished by anchoring the delivery device to the skin using adhesives or by using anchored microprojections, such as described in WO 97/48440, incorporated by reference in its entirety.

FIG. 11 illustrates one embodiment of a stratum corneum-piercing microprojection transdermal delivery device for use with the present invention. FIG. 11 shows a portion of a device 10 having a plurality of microprojections 12. The microprojections 12 extend at substantially a 90° angle from a sheet 14 having openings 16. The sheet 14 may be incorporated in a delivery patch including a backing for the sheet 14 and may additionally include adhesive for adhering the patch to the skin. In this embodiment, the microprojections are formed by etching or punching a plurality of microprojections from a thin metal sheet and bending the microprojections out of a plane of the sheet. Metals such as stainless steel and titanium are preferred. Metal microprojections are disclosed in Trautman et al, U.S. Pat. No. 6,083,196; Zuck U.S. Pat. No. 6,050,988; and Daddona et al., U.S. Pat. No. 6,091, 975; the disclosures of which are incorporated herein by reference. Other microprojections that can be used with the present invention are formed by etching silicon using silicon chip etching techniques or by molding plastic using etched micro-molds. Silicon and plastic microprojections are disclosed in Godshall et al., U.S. Pat. No. 5,879,326, the disclosures of which are incorporated herein by reference.

FIG. 12 illustrates the microprojection transdermal delivery device having microprojections 12 having a biologically active agent-containing coating 18. The coating 18 may partially or completely cover the microprojections. For example, the coating can be in a dry pattern coating on the microprojections. The coatings can be applied before or after the microprojections are formed.

The coating on the microprojections can be formed by a variety of known methods. One such method is dip-coating. Dip-coating can be described as a means to coat the microprojections by partially or totally immersing the microprojections into the drug-containing coating solution. Alternatively the entire device can be immersed into the coating solution. Coating only those portions the microprojection that pierces the skin is preferred.

By use of the partial immersion technique described above, it is possible to limit the coating to only the tips of the microprojections. There is also a roller coating mechanism that limits the coating to the tips of the microprojection. This technique is described in a U.S. patent application Ser. No. 10/099,604, filed 15 Mar. 2002, which is fully incorporated herein by reference.

Other coating methods include spraying the coating solution onto the microprojections. Spraying can encompass formation of an aerosol suspension of the coating composition. In a preferred embodiment an aerosol suspension forming a droplet size of about 10 to 200 picoliters is sprayed onto the microprojections and then dried. In another embodiment, a very small quantity of the coating solution can be deposited onto the microprojections as a pattern coating 18. The pattern coating 18 can be applied using a dispensing system for positioning the deposited liquid onto the microprojection surface. The quantity of the deposited liquid is preferably in the range of 0.5 to 20 nl/microprojection. Examples of suitable precision metered liquid dispensers are disclosed in U.S. Pat. Nos. 5,916,524; 5,743,960; 5,741,554; and 5,738,728, the disclosures of which are incorporated herein by reference. Microprojection coating solutions can also be applied using ink jet technology using known solenoid valve dispensers, optional fluid motive means and positioning means which is generally controlled by use of an electric field. Other liquid dispensing technology from the printing industry or similar liquid dispensing technology known in the art can be used for applying the pattern coating of this invention.

In all cases, after a coating has been applied, the coating solution is dried onto the microprojections by various means. In a preferred embodiment the coated device is dried in ambient room conditions. However, various temperatures and humidity levels can be used to dry the coating solution onto the microprojections. Additionally, the devices can be heated, lyophilized, freeze dried or similar techniques used to remove the water from the coating.

A number of factors affect the volatility of compounds. These include temperature, atmospheric pressure, and vapor pressure of the compound. The volatilization process is time dependant. In addition, ionized compounds present a much lower volatility as compared to their unionized forms. For example, acetic acid has a boiling point of 118° C. while sodium acetate is essentially non-volatile. If a volatile compound in equilibrium between its ionized and non-ionized forms is present in a solution, only the non-ionized form disappears from the solution and the ionized form stays in solution.

If the volatile compound is a weak acid AH the following equilibrium takes place in solution:

$$AH \Leftrightarrow A^- + H^+$$

With Ka1 being the equilibrium constant for AH, the equilibrium can be written as:

$$Ka1 = (A^-) \times (H^+)/(AH)$$

$(A^-)$, $(H^+)$ and $(AH)$ represent the concentrations of the species present in solution.

If AH is volatile, the equilibrium will shift towards $A^- + H^+ \Rightarrow AH$ in order to satisfy the laws of equilibrium. Ultimately, the entire mass of the volatile weak acid will disappear from the solution.

If the volatile compound is a weak base (B) the following equilibrium takes place:

$$B + H^+ \Leftrightarrow BH^+$$

With Ka2 being the equilibrium constant, the equilibrium can be written as:

$$Ka2 = (B) \times (H^+)/(BH^+)$$

$(B)$, $(H^+)$, and $(BH^+)$ represent the concentrations of the species present in solution.

If B is volatile, the equilibrium will shift towards $BH^+ \Rightarrow B + H^+$ in order to satisfy the laws of equilibrium. Ultimately, the entire mass of the volatile weak base will disappear from the solution.

When a weak acid and a weak base are mixed in solution, they form a salt according to the following equilibrium:

$$AH + B \Leftrightarrow A^- + BH^+$$

With Ka1 and Ka2 representing the equilibrium constants for AH and B, respectively, the equilibrium can be written as:

$$Ka1/Ka2 = (A^-) \times (BH^+)/(AH) \times (B).$$

If AH is volatile, the equilibrium will shift towards $A^- + BH^+ \Rightarrow AH + B$ in order to satisfy the laws of equilibrium. The net result will be an increase in the concentration of the free base and a resulting increase in pH.

Conversely, if B is volatile, the equilibrium will shift identically with a net result of an increase in the concentration of the free acid and a decrease in pH. Strong acids present a particular case because many of them are highly volatile. Indeed, hydrochloric acid is a gas in ambient conditions. When combined with a base, they form non-volatile salts because they are completely ionized in a wide pH range with the exception of extreme pH for some acids. In solution, or in the solid state, volatilization of the counterion occurs at the interface between the solution and the atmosphere or the solid and the atmosphere. In a solution, the high diffusivity of solutes minimizes differences in concentration between the interface and the bulk of the solution.

Figure 10:
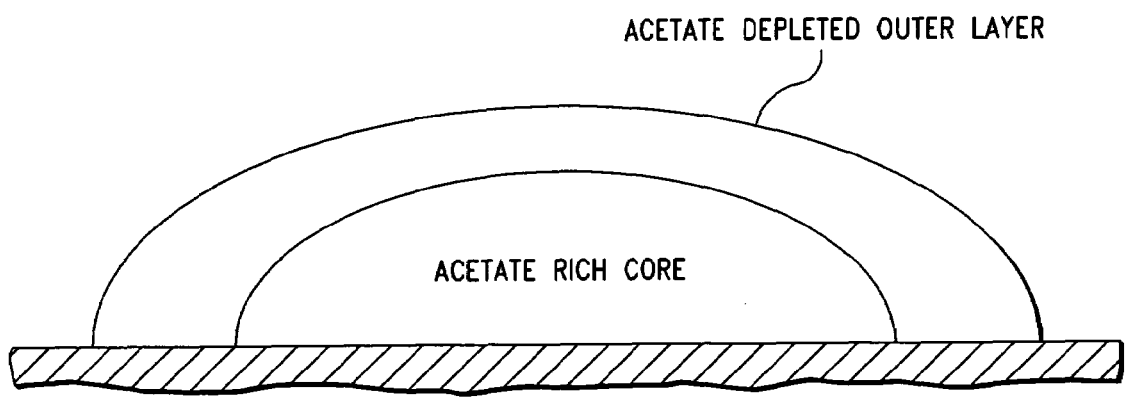
FIG. 10 is a diagram showing the depicting the loss of volatile counterion from the outer layer of a coating.

Conversely, in a solid state, diffusivity is very slow or non-existent and greater concentration gradients of the volatile counterion are achieved between the interface and the bulk of the solution. Ultimately, the outer layer of the coating is depleted in counterion while the bulk of the solid coating is relatively unchanged as compared to the initial dry state (see FIG. 10). This situation may results in a highly insoluble outer coating if the counterion is associated with a drug that is substantially insoluble in its neutral net charge state. Indeed, as will be explained in detail in Example 1, volatilization of the counterion results in formation of the water insoluble neutral species. This, in turn, jeopardizes dissolution of the drug from the solid coating upon exposure to the biological fluids.

Other known formulation adjuvants can be added to the coating solution as long as they do not adversely affect the necessary solubility and viscosity characteristics of the coating solution and the physical integrity of the dried coating.

Generally, in the noted embodiments of the invention, the amount of counterion should neutralize the charge of the biologically active agent. In such embodiments, the counterion or the mixture of counterion is present in amounts necessary to neutralize the charge present on the agent at the pH of the formulation. Excess of counterion (as the free acid or as a salt) can be added to the peptide in order to control pH and to provide adequate buffering capacity.

In another preferred embodiment the counterion is a strong acid. Strong acids can be defined as presenting at least one pKa lower than about 2. Examples of such acids include hydrochloric acid, hydrobromic acid, nitric acid, sulfonic acid, sulfuric acid, maleic acid, phosphoric acid, benzene sulfonic acid and methane sulfonic acid.

Another preferred embodiment is directed to a mixture of counterions wherein at least one of the counterion is a strong acid and at least one of the counterion is a low volatility weak acid.

Another preferred embodiment is directed to a mixture of counterions wherein at least one of the counterions is a strong acid and at least one of the counterion is a weak acid with high volatility. Volatile weak acid counterions present at least one pKa higher than about 2 and a melting point lower than about 50° C. or a boiling point lower than about 170° C. at $P_{atm}$. Examples of such acids include acetic acid, propionic acid, pentanoic acid and the like.

The acidic counterion is present in amounts necessary to neutralize the positive charge present on the drug at the pH of the formulation. Excess of counterion (as the free acid or as a salt) can be added to the drug in order to control pH and to provide adequate buffering capacity.

In one embodiment of the invention, the coating formulations include at least one antioxidant, which can be sequestering agents such sodium citrate, citric acid, EDTA (ethylene-dinitrilo-tetraacetic acid) or free radical scavengers such as ascorbic acid, methionine, sodium ascorbate, and the like. Presently preferred antioxidants include EDTA and methionine.

In one embodiment of the invention, the coating formulation includes at least one surfactant, which can be zwitterionic, amphoteric, cationic, anionic, or nonionic, including, without limitation, sodium lauroamphoacetate, sodium dodecyl sulfate (SDS), cetylpyridinium chloride (CPC), dodecyltrimethyl ammonium chloride (TMAC), benzalkonium, chloride, polysorbates such as TWEEN® 20 and TWEEN® 80, other sorbitan derivatives, such as sorbitan laurate, and alkoxylated alcohols, such as laureth-4.

In a further embodiment of the invention, the coating formulation includes at least one polymeric material or polymer that has amphiphilic properties, which can comprise, without limitation, cellulose derivatives, such as hydroxyethylcellulose (HEC), hydroxypropylmethylcell-ulose (HPMC), hydroxypropycellulose (HPC), methylcellulose (MC), hydroxyethylmethylcellulose (HEMC), or ethylhydroxy-ethylcellulose (EHEC), as well as PLURONIC® type copolymers.

In another embodiment, the coating formulation includes a hydrophilic polymer selected from the following group: hydroxyethyl starch, dextran, poly(vinyl alcohol), poly(ethylene oxide), poly(2-hydroxyethylmethacrylate), poly(n-vinyl pyrolidone), polyethylene glycol and mixtures thereof, and like polymers.

In another embodiment of the invention, the coating formulation includes a biocompatible carrier, which can comprise, without limitation, human albumin, bioengineered human albumin, polyglutamic acid, polyaspartic acid, polyhistidine, pentosan polysulfate, polyamino acids, sucrose, trehalose, melezitose, raffinose and stachyose.

In another embodiment, the coating formulation includes a stabilizing agent, which can comprise, without limitation, a non-reducing sugar, a polysaccharide or a reducing sugar. Suitable non-reducing sugars for use in the methods and compositions of the invention include, for example, sucrose, trehalose, stachyose, or raffinose. Suitable polysaccharides for use in the methods and compositions of the invention include, for example, dextran, soluble starch, dextrin, and insulin. Suitable reducing sugars for use in the methods and compositions of the invention include, for example, monosaccharides such as, for example, apiose, arabinose, lyxose, ribose, xylose, digitoxose, fucose, quercitol, quinovose, rhamnose, allose, altrose, fructose, galactose, glucose, gulose, hamamelose, idose, mannose, tagatose, and the like; and disaccharides such as, for example, primeverose, vicianose, rutinose, scillabiose, cellobiose, gentiobiose, lactose, lactulose, maltose, melibiose, sophorose, and turanose, and the like.

In another embodiment, the coating formulation includes a vasoconstrictor, which can comprise, without limitation, amidephrine, cafaminol, cyclopentamine, deoxyepinephrine, epinephrine, felypressin, indanazoline, metizoline, midodrine, naphazoline, nordefrin, octodrine, ornipressin, oxymethazoline, phenylephrine, phenylethanolamine, phenylpropanolamine, propylhexedrine, pseudoephedrine, tetrahydrozoline, tramazoline, tuaminoheptane, tymazoline, vasopressin, xylometazoline and the mixtures thereof. The most preferred vasoconstrictors include epinephrine, naphazoline, tetrahydrozoline indanazoline, metizoline, tramazoline, tymazoline, oxymetazoline and xylometazoline.

As will be appreciated by one having ordinary skill in the art, the addition of a vasoconstrictor to the coating formulations and, hence, solid biocompatible coatings of the invention is particularly useful to prevent bleeding that can occur following application of the microprojection device or array and to prolong the pharmacokinetics of the active agent through reduction of the blood flow at the application site and reduction of the absorption rate from the skin site into the system circulation.

In another embodiment of the invention, the coating formulation includes at least one "pathway patency modulator", which can comprise, without limitation, osmotic agents (e.g., sodium chloride), zwitterionic compounds (e.g., amino acids), and anti-inflammatory agents, such as betamethasone 21-phosphate disodium salt, triamcinolone acetonide 21-disodium phosphate, hydrocortamate hydrochloride, hydrocortisone 21-phosphate disodium salt, methylprednisolone 21-phosphate disodium salt, methylprednisolone 21-succinaate sodium salt, paramethasone disodium phosphate and prednisolone 21-succinate sodium salt, and anticoagulants, such as citric acid, citrate salts (e.g., sodium citrate), dextrin sulfate sodium, aspirin and EDTA.

In yet another embodiment of the invention, the coating formulation includes a solubilizing/complexing agent, which can comprise Alpha-Cyclodextrin, Beta-Cyclodextrin, Gamma-Cyclodextrin, glucosyl-alpha-Cyclodextrin, maltosyl-alpha-Cyclodextrin, glucosyl-beta-Cyclodextrin, maltosyl-beta-Cyclodextrin, hydroxypropyl beta-cyclodextrin, 2-hydroxypropyl-beta-Cyclodextrin, 2-hydroxypropyl-gamma-Cyclodextrin, hydroxyethyl-beta-Cyclodextrin, methyl-beta-Cyclodextrin, sulfobutylether-alpha-cyclodextrin, sulfobutylether-beta-cyclodextrin, and sulfobutylether-gamma-cyclodextrin. Most preferred solubilizing/complexing agents are beta-cyclodextrin, hydroxypropyl beta-cyclodextrin, 2-hydroxypropyl-beta-Cyclodextrin and sulfobutylether7 beta-cyclodextrin.

In another embodiment of the invention, the coating formulation includes at least one non-aqueous solvent, such as ethanol, isopropanol, methanol, propanol, butanol, propylene glycol, dimethysulfoxide, glycerin, N,N-dimethylformamide and polyethylene glycol 400.

Preferably, the coating formulations have a viscosity less than approximately 500 centipoise and greater than approximately 3 centipoise.

In one embodiment of the invention, the thickness of the biocompatible coating is less than 25 microns, more preferably, less than 10 microns, as measured from the microprojection surface.

The following examples are given to enable those skilled in the art to more clearly understand and practice the present invention. They should not be considered as limiting the scope of the invention but merely as being illustrated as representative thereof. A method has been devised to calculate the distribution of ionic species in polypeptides and other electrolytes. Equations for equilibrium calculations have been available for many years. They are based on the classic equilibrium laws. They can be used successfully to calculate the net charge of polyelectrolytes such as polypeptides as well as the pI of a protein. Net charge and pI calculations are powerful tools for characterizing and purifying polypeptides. Nevertheless, these calculations do not yield direct information about the species present in solution at a specific pH. For example, the pH range in which species with suspected low solubility are present are not predicted from these methods. Various attempts have been made to estimate the equilibria between different ionic forms in polyelectrolytes. These attempts have been summarized by Edsall J. T. (Proteins as acids and bases, in proteins, amino acids and peptides as ions and dipolar ions, Cohn E. J. & Edsall J. T. eds; Hafner Pub; New York and London, 1943, 444-505).

The most successful approach describes a probability distribution function for a system of independently ionizing groups. In this treatment, the various groups are classified by classes, each corresponding to one pKa value. The procedure is somewhat cumbersome and is not easily amenable to automatic computation. In addition, calculations are limited to the net charged species and do not include description of the charge distribution within the molecule. Surprisingly, with polyelectrolytes, very little attention has been paid to the concentrations of the actual species that are present in solution. This seems to be the result of the lack of equations describing the distribution of species in the presence of overlapping $pK_a$ values, that is, two or more $pK_a$ values separated by less than about 3 pH units. In this case, approximations are being used to calculate the distribution of the species. In a polypeptide molecule, where more than ten overlapping $pK_a$ values is commonplace, computations based on these approximations are not practical and would certainly yield erroneous results. As a result, distribution of species in polypeptides apparently has not been described. A method has been devised that provides equations describing the species distribution for any polyelectrolyte, provided that their $pK_a$ values are known. A computational algorithm for performing these calculations is also provided.

Methods

For polypeptides, the acid-base radicals implicated and their $pK_a$ values are, respectively: terminal carboxyl, $pK_a=3.05$; β-carboxyl of aspartate, $pK_a=3.93$; γ-carboxyl of glutamate, $pK_a=4.43$; thiol of cysteine, $pK_a=8.38$; phenol of tyrosine, $pK_a=10.36$; imidazolium of histidine, $pK_a=5.96$; terminal ammonium, $pK_a=8.1$; ε-ammonium of lysine, $pK_a=10.59$; guanidinium of arginine, $pK_a=12.48$. The above $pK_a$ values are averages compiled from the literature and used in the examples. The pI values were extrapolated from the net charge profile of the molecule calculated from their $pK_a$ values.

Determination of the Species Concentrations in a Polyelectrolyte:

For a weak acid, AH, the equilibrium can be written $$AH \rightleftharpoons A^- + H^+$$

Its dissociation constant being:

$$K_a = (A^-) \times (H^+)/(AH)$$

$(A^-)$, $(H^+)$, and $(AH)$ being the respective concentrations of the species.

From the above, the classic Henderson-Hasselbalch equation can be derived:

$$pH = pK_a + \mathrm{Log}((A^-)/(AH))$$

Assuming that: $(A^-)+(AH)=1$, this equation yields:

Mole fraction neutral $= 1/(1+10^{pH-pKa}) = P$ which can also be defined as the probability of the acid to be neutral. Similarly:

Mole fraction ionized, negatively charged $= 1-1/(1+10^{pH-pKa}) = 1-P$

Net charge $= 1/(1+10^{pH-pKa}) - 1$

For a weak base, B, the equilibrium can be written:

$$B + H^+ \rightleftharpoons BH^+$$

Its dissociation constant being:

$$K_a = (B) \times (H^+)/(BH^+)$$

Similarly:

$$pH = pK_a - \mathrm{Log}(BH^+/B),$$

Mole fraction neutral $= 1/(1+10^{pKa-pH}) = Q$

Mole fraction ionized, positively charged $= 1-1/(1+10^{pKa-pH}) = 1-Q$

Net charge $= 1 - 1/(1+10^{pKa-pH})$

The species are defined as all the possible combinations of the charges for the acidic functions and basic functions of the compound in solution. For example if the compound presents only acidic functions, the species take the values like $0^-$, $1^-$, $2^-$, and etc. Similarly, if the compound presents only basic functions, the species take the values like $0^+$, $1^+$, $2^+$, and etc. If the compound has both acidic and basic functions, then the species take the values of $0^-0^+$, $0^-1^+$, $1^-0^+$, $1^-1^+$, etc. The net charged species are defined as the sum of all species presenting an identical net charge. They take the values: . . . −2, −1, 0, +1, +2 . . . .

For a compound bearing one acidic (negatively charged) $pK_a$, the species present in solution at any pH are: $0^-$ and $1^-$ (one species is neutral: no positive charge and no negative charge; the other species has one negative charge and no negative charge). $P_1$ being the probability of the acidic group to be neutral, the mole fraction of these species at a specific pH is:

$0^-$: $P_1$
$1^-$: $1-P_1$

For a compound bearing one acidic $pK_a$, and one basic (positively charged) $pK_a$, the species present in solution at a specific pH are: $0^-0^+$, $0^-1^+$, $1^-0^+$, $1^-1^{+1}$.

$P_1$ and $Q_1$ being the probability of the acidic and basic group, respectively, to be neutral, the mole fraction of these species at a specific pH is:

$0^-0^+$: $P_1 \times Q_1$
$0^-1^+$: $P_1 \times (1-Q_1)$
$1^-0^+$: $(1-P_1) \times Q_1$
$1^-1^+$: $(1-P_1) \times (1-P_1)$ For a compound bearing one acidic $pK_a$, and two basic $pK_a$, the species present in solution at any pH are: $0^-0^+$, $0^-1^+$, $0^-2^+$, $1^-0^+$, $1^-1^+$, $1^-2^+$.

$P_1$ being the probability of the acidic groups to be neutral, and $Q_1$ and $Q_2$ being the probabilities of the basic groups to be neutral, the mole fraction of these species at a specific pH is:

$0^-0^+$: $P_1 \times Q_1 \times Q_2$
$0^-1^+$: $(P_1 \times Q_1 \times (1-Q_2)) + (P_1 \times (1-Q_1) \times Q_2)$
$0^-2^+$: $P_1 \times (1-Q_1) \times (1-Q_2)$
$1^-0^+$: $(1-P_1) \times Q_1 \times Q_2$
$1^-1^+$: $((1-P_1) \times Q_1 \times (1-Q_2)) + ((1-P_1) \times (1-Q_1) \times Q_2)$
$1^-2^+$: $(1-P_1) \times \times (1-Q_1) \times (1-Q_2)$
Etc. . . .

As can be seen, there are (N+1) (M+1) species, N and M being the number of acidic and basic $pK_a$, respectively. In the previous example, there were six possible species. The possible net charged species, which are −1, 0, +1, +2. The number of possible net charged species is (N+M+1). The mole fraction of these net charged species at a specific pH can be easily deduced. Using the preceding example:

−1: $(1-P_1) \times Q_1 \times Q_2$
0: $(P_1 \times Q_1 \times Q_2) + ((1-P_1) \times Q_1 \times (1-Q_2)) + ((1-P_1) \times (1-Q_1) \times Q_2)$
+1: $(P_1 \times Q_1 \times (1-Q_2)) + (P_1 \times (1-Q_1) \times Q_2) + (1-P_1) \times \times (1-Q_1) \times (1-Q_2)$
+2: $P_1 \times (1-Q_1) \times (1-Q_2)$ Computational Algorithm of the Species and Valences of a Polyelectrolyte:

Based on the above equations, an algorithm has been derived which is used to calculate the charge, net charge, species and valences present in a polyelectrolyte. In the following, a bold and upper letter to denote a vector or a matrix, and a lower letter represent an element of the vector or the matrix.

Suppose we know that there are N acidic functions and M basic functions in the compound, their $pK_a$ values are given, and the pH value of the solution is also given. Let $PKA_a$ be the N by 1 vector of acidic $pK_a$ values, and $PKA_b$ be the M by 1 vector of basic $pK_a$ values:

$PKA_a = (pKa_{a1}, pKa_{a2}, \ldots, pKa_{aN})^T$
$PKA_b = (pKa_{b1}, pKa_{b2}, \ldots, pKa_{bM})^T$
$P = (p_1, p_2, \ldots, p_N)^T$
$Q = (q_1, q_2, \ldots, q_M)^T$ $$p_i = 1/(1+10^{pH-pKa_{ai}}) \quad (1)$$

$$q_j = 1/(1+10^{pKa_{bj}-pH}) \quad (2)$$

where P and Q are mole fraction neutral for acidic components and basic functions, respectively. They also can be understood as the probabilities of being neutral for either acid or base. Let $CHARGE_a$ denote the N by 1 vector of charge for the acids, while $CHARGE_b$ is the M by 1 vector for the bases:

$CHARGE_a = (charge_{a1}, charge_{a2}, \ldots, charge_{aN})^T$
$CHARGE_b = (charge_{b1}, charge_{b2}, \ldots, charge_{bM})^T$ $$charge_{ai} = 1/(1+10^{pH-pKa_{ai}}) - 1 \quad (3)$$

$$charge_{bj} = 1 - 1/(1+10^{pKa_{bj}-pH}) \quad (4)$$

$$\text{net charge} = \sum_{i=1}^{N} charge_{ai} + \sum_{j=1}^{M} charge_{bj} \quad (5)$$

where net charge is the charge of the complex molecule in the solution.

Next, let us consider the species of the molecule compound. For simplicity, we will use α to represent the species. In order to understand the species calculation algorithm, let's start from the simple case. Suppose the compound only has N acids, we want the probabilities of α in the solution. Based on the above derivation, P is the probability vector for the acids being neutral. Let us consider a statistical experiment. Suppose that the compound in the solution is made by adding one acid by one acid. At the beginning, when only one acid is in the solution, we have:

$$\text{Prob}(\alpha=0^-, 1 \text{ acid}) = p_1 \quad (6)$$

$$\text{Prob}(\alpha=1^-, 1 \text{ acid}) = 1 - p_1 \quad (7)$$

$$\text{Prob}(\alpha=2^-, 1 \text{ acid}) = \ldots =$$

$$= \text{Prob}(\alpha=N^-, 1 \text{ acid}) = 0 \quad (8)$$

Then given that we already have i acids in the solution, and add one more thereafter. The relationships of the probabilities are:

$\text{Prob}(\alpha=0^-, i+1 \text{ acids})$ $= \text{Prob}(\alpha=0^-, i \text{ acids} | \text{the } (i+1)\text{th acid}=0)\text{Prob}(\text{the } i+1\text{th acid}=0)$ $\text{Prob}(\alpha=j^-, i+1 \text{ acids})$ $= \text{Prob}(\alpha=j^-, i \text{ acids} | \text{the } (i+1)\text{th acid}=0)\text{Prob}(\text{the } i+1\text{th acid}=0)$ $+ \text{Prob}(\alpha=(j-1)^-, i \text{ acids} | \text{the } (i+1)\text{th acid}=1)\text{Prob}(\text{the } i+1\text{th acid}=1)$ Here we are making an assumption that all the acids are independent, hence we can rewrite the above equations:

$\text{Prob}(\alpha=0^-, i+1 \text{ acids})$ $$= \text{Prob}(\alpha=0^-, i \text{ acids})\text{Prob}(\text{the } i+1\text{th acid}=0) \quad (9)$$

$\text{Prob}(\alpha=j^-, i+1 \text{ acids})$ $= \text{Prob}(\alpha=j^-, i \text{ acids})\text{Prob}(\text{the } i+1\text{th acid}=0)$ $$+ \text{Prob}(\alpha=(j-1)^-, i \text{ acids})\text{Prob}(\text{the } i+1\text{th acid}=1) \quad (10)$$

Equation (9) and (10) give us an easy way to calculate the probabilities. To implement them, let R be a N+1 by N matrix:

$r[j,i] = \text{Prob}(\alpha=(j-1)^-, i \text{ acids})$

We can rewrite (6), (7), (8), (9) and (10) as:

$$r[1,1] = P_1 \quad (11)$$

$$r[2,1] = 1 - P_1 \quad (12)$$

$$r[3,1] = \ldots = r[N+1,1] = 0 \quad (13)$$

$$r[1,i+1] = r[1,i]p_{i+1} \quad (14)$$

$$r[j+1,i+1] = r[j+1,i]p_{i+1} + r[j,i](1-p_{i+1}) \quad (15)$$

$i = 1 \ldots (N-1), j = 1, \ldots, N$

It is very straightforward to code the above recursion algorithm by loops, and the last column of R simply represents the probabilities of species when a compound with N acids is in the solution. Without losing of the generality, let A be the last column of R. Similarly let B be the species probability vector when a compound of M bases is in the solution, and the dimension is M+1 by 1. The calculation of B follows the same rule as A. If the compound has N acids and M bases, the probabilities of species are:

$$C = A \times B^T \quad (16)$$

$$c[i,j] = \text{Prob}(\alpha=(i-1)^-(j-1)^+) \quad (17)$$

$i = 1, 2, \ldots, N+1$ $j = 1, 2, \ldots, M+1$ where C is an N+1 by M+1 matrix. At last, the net charged species (β) can be constructed based on C:

$$\text{Prob}(\beta = i) = \sum_{\substack{i=k-j \\ k=1,\ldots,M+1 \\ j=1,\ldots,N+1}} c[j,k] \quad (18)$$

where $i = -N, \ldots, -1, 0, 1, \ldots, M$

Based on the above, the distribution of charged or neutral species for selected compounds can be calculated, which is illustrated in the following examples.

Example 1

FIG. 1 shows the charge profile of acetic acid (pKa 4.75) as a function of pH. At pH below about 2.5 the carboxyl group of the acetic acid is completely protonated and thus there is no charge on the molecule. As the pH increases from about 2.5 to about 7, more and more of the carboxyl moieties become ionized and thus forming the negatively charged acetate ion. At about pH 7, all of the carboxyl groups are ionized.

Figure 2:
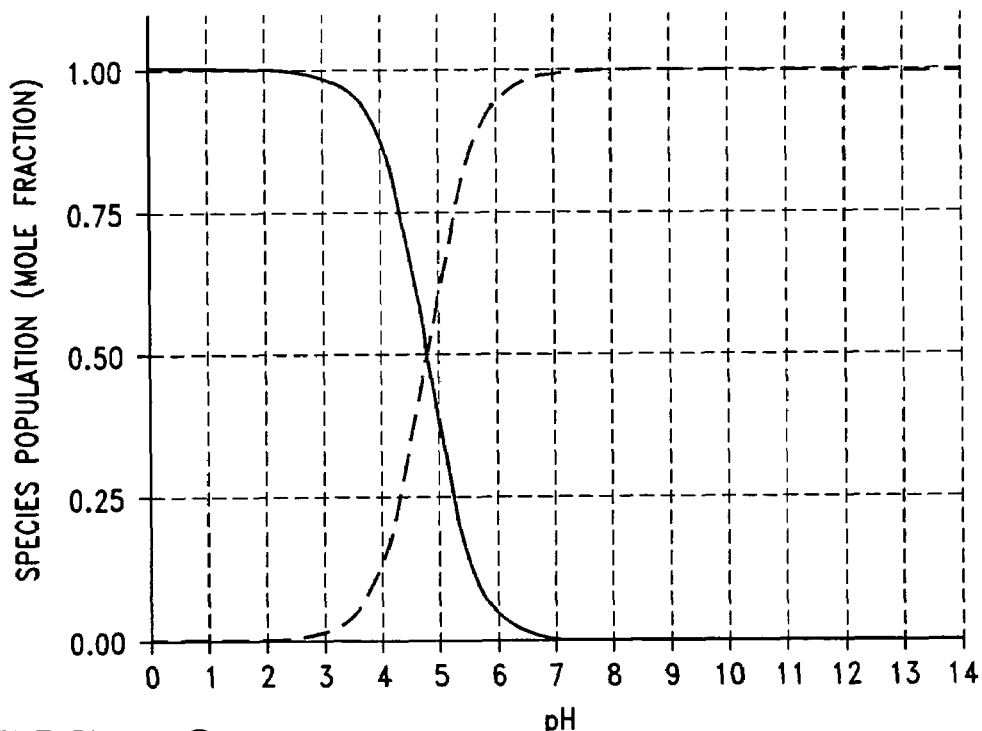
FIG. 2 is a graph showing the mole ratios of uncharged acetic acid and charged acetate ion as a function of pH.

FIG. 2 shows the mole ratios of acetic acid and acetate. At pH 0, with the carboxyl group of acetic acid fully protonated, there essentially only acetic acid, thus the mole fraction is 1. At about ph 2.5, there ionization of the carboxyl group begins and the solid curve representing acetic acid in graph starts to move downward. At the same time, the dashed line, representing the ionized acetate, starts to move upwards off of the 0.00 line. At about pH 4.7 there are equal numbers of charged and uncharged moieties. At pH greater than about 7, there is no longer any uncharged acetic acid and essentially all of species are the charged acetate ion.

Many drugs exhibit maximum solubility in water when they are in an electrically charged state. FIG. 3 shows the charge profile of fentanyl, a small molecular weight weakly basic drug presenting one basic pKa, 8.5. At pH below 6, essentially all of the fentanyl is positively charged, while at pH above 11, essentially all of the fentanyl is neutral.

FIG. 4 shows the mole ratios of the neutral (Fentanyl base-solid line) and charged fentanyl (Fentanyl$^{+1}$-dashed line) species at different pHs. From pH 0 to about pH 6, there is essentially no Fentanyl base present and 100% is the charged Fentanyl$^{+1}$. From pH about 6 to about pH 11, there is a transition. The Fentanyl$^{+1}$ decreases at the same rate that the Fentanyl base increases. At or above pH 11, essentially all of the Fentanyl exists in the non-charged, neutral, Fentanyl base.

Figure 5:
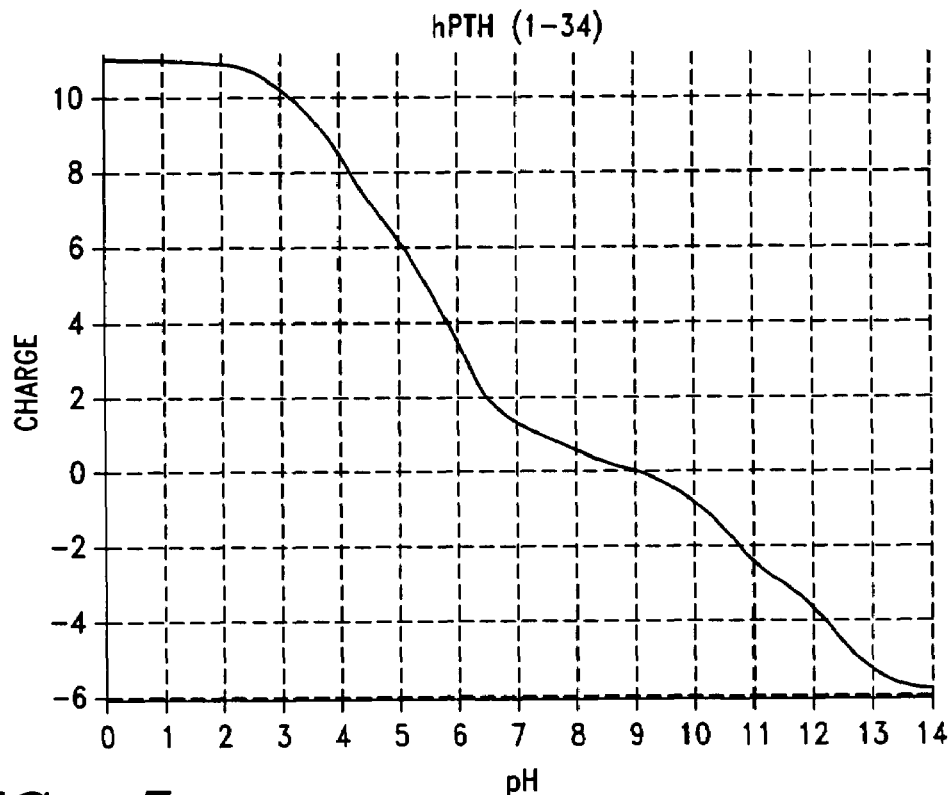
FIG. 5 is a graph showing the charge profile of hPTH(1-34) as a function of pH.

Complex molecules such as peptides and proteins also exhibit charge characteristics that are dependant on pH. FIG. 5 shows the charge profile of hPTH(1-34), a peptide presenting 11 basic pKa's, and six acidic pKa's. At pH 9, the peptide presents a zero net electric charge. This point is also called the isoelectric point or pI.

Figure 6:
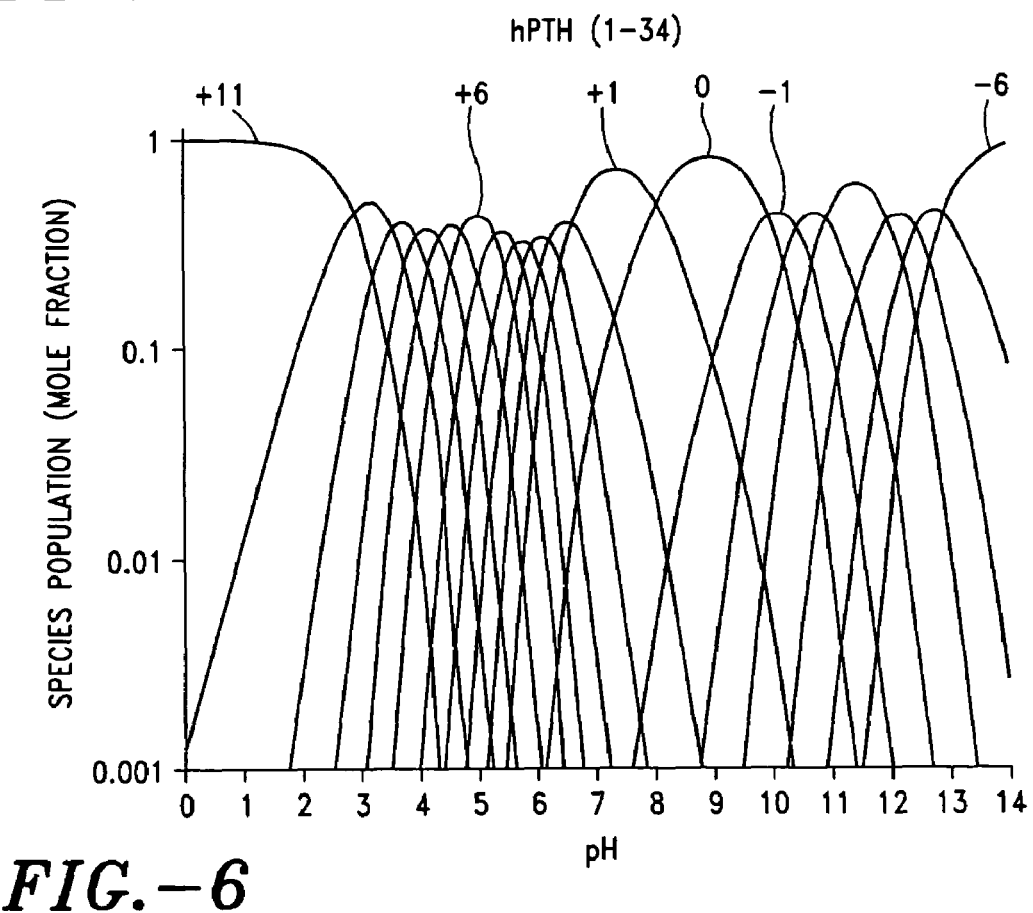
FIG. 6 is a graph showing the mole ratios of the net charged species of hPTH(1-34) as a function of pH.

FIG. 6 shows the mole ratios of the net charged species of PTH. The species range from a +11 charge to a −6 charge. The neutral species only exist in significant amounts in the pH range of about 6 to about 11.5. In this pH range, PTH precipitates out of solution.

Figure 7:
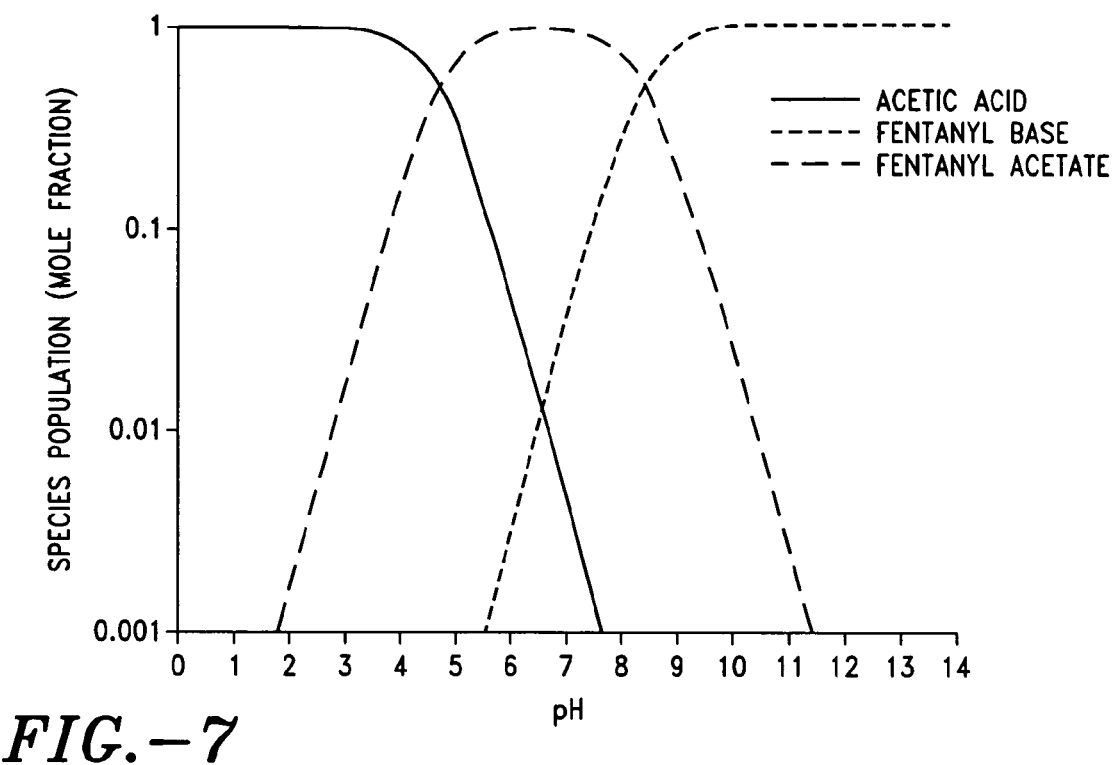
FIG. 7 is a graph showing the mole ratios of fentanyl acetate, acetic acid and the neutral form of fentanyl (Fentanyl base) as a function of pH.

FIG. 7 shows the mole ratios for fentanyl acetate (dashed line), acetic acid (solid line), and the neutral form of fentanyl (fentanyl base-dotted line). These are the species that are present in solution at different pH's when various ratios of fentanyl base and acetic acid are mixed in solution. The pH of fentanyl acetate (mole ratio 1 to 1) in solution is predicted to be about 6.6. At that pH, about 1% of fentanyl is present as fentanyl base, which, for a 10 mg/mL solution total fentanyl, would be at or above the limit of solubility of the base, which would therefore precipitate out. Solubilization can be achieved by supplementing the formulation with excess acetic acid, which will result in acidification of the formulation and will therefore results in a decrease in the amount of fentanyl base. Nevertheless, during drying and subsequent storage the free acetic acid will evaporate which will ineluctably result in the formation of the water insoluble base. Subsequent reconstitution in water would not allow total solubilization of fentanyl. The use of a non-volatile counterion would provide a solid soluble formulation of fentanyl as long as the pH is maintained at least 2 pH units, preferably 3 pH units, below the pKa of fentanyl. This could be achieved by providing at least a slight excess of non-volatile counterion to the formulation (ie. a mole ration of non-volatile counterion to fentanyl slightly greater than 1:1). In addition, volatile counterions could be added to that formulation without affecting the solubility of the dry coating.

Figure 8:
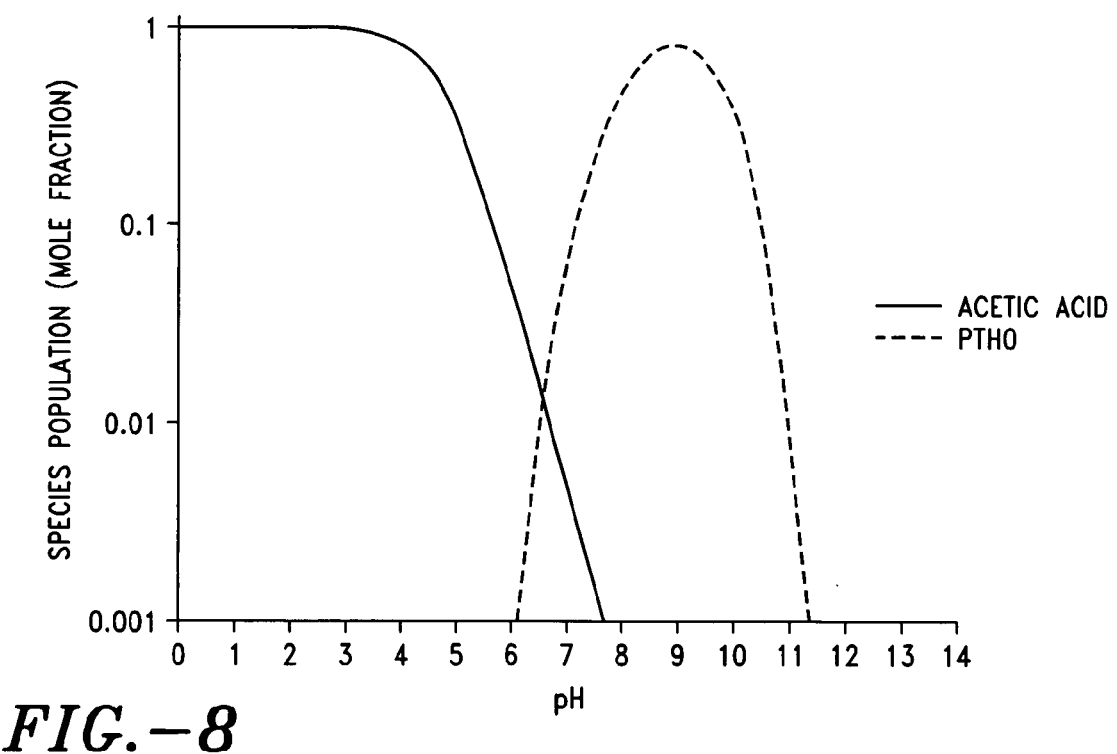
FIG. 8 is a graph showing the mole ratios for acetic acid the net neutral form of hPTH(1-34) as function of pH.

FIG. 8 shows the mole ratios for acetic acid (solid line) and the neutral form of hPTH(1-34) (dotted line). The pH of a hPTH(1-34) hexaacetate (mole ratio 1 to 6) in solution is predicted to be about 5 (see FIG. 5). At that pH, negligible amounts of hPTH(1-34) are present as hPTH(1-34) zero net charge (PTH 0—see the charge curve for the "0" charge species in FIG. 6) and hPTH(1-34) is highly soluble in water at concentrations in excess of 20%. As in the case of fentanyl, during drying and subsequent storage, the volatile free acetic acid will evaporate which will result in a shift to a higher pH, which results in formation of the water insoluble PTH 0. Subsequent reconstitution in water would not allow total solubilization of hPTH(1-34). The use of a non-volatile counterion would provide a solid soluble formulation of hPTH(1-34) as long as the pH is maintained at least 2.5 pH units, preferably 3 pH units, below the pI of hPTH(1-34). This could be achieved by providing at least about 2 non-volatile counterions to each molecule of hPTH(1-34). As in the case of fentanyl, volatile counterions could be added to that formulation without affecting the solubility of the dry coating.

Example 2

Several aqueous formulations containing hPTH(1-34) were prepared. These formulations contained the volatile counterion acetic acid. Several formulations contained additional non-volatile counterions hydrochloric acid, glycolic acid, or tartaric acid (see Table 1). Microprojection arrays (microprojection length 200 μm, 595 microprojections per array) had a skin contact area 2 cm$^2$. The tips of the microprojections were coated with these formulations by passing the arrays over a rotating drum carrying the hPTH(1-34) formulations using the method and apparatus disclosed in U.S. patent application Ser. No. 10/099,604 filed Mar. 15, 2002, which is hereby incorporated by reference in its entirety. Four successive coatings were performed on each microprojection array at 2-8° C. The amount of peptide coated on the arrays was evaluated by ultraviolet spectroscopy at a wavelength of 275 nm. Scanning electron microscopy revealed that the solid coating had a very smooth surface with no evidence of cracking. Furthermore good uniformity of coating from microprojection to microprojection was observed, with the coating limited to the first 100 μm of the microprojection tip. Some of the tip-coated arrays were subsequently used for drug delivery studies in hairless guinea pigs (HGPs).

The HGPs were anesthetized by intramuscular injection of xylazine (8 mg/kg) and ketamine HCl (44 mg/kg). The anesthetized HGPs were catheterized through the carotid artery. The catheter was flushed with heparinized saline (20 IU/mL) to prevent clotting. Animals were maintained under anesthesia throughout the experiment via injection of sodium pentobarbital (32 mg/mL) directly into the catheter (0.1 mL/injection). Before application of the coated microprojection arrays, blood samples were taken into heparinized vials (final concentration of heparin at 15 IU/mL), which served as 0 or baseline samples.

The application of the coated microprojection arrays was performed on the flank of the anesthetized animals with a spring-driven impact applicator (total energy=0.4 Joules, delivered in less than 10 milliseconds), the type disclosed in U.S. patent application Ser. No. 09/976,798 filed Oct. 12, 2001, which is hereby incorporated by reference in its entirety. The system applied comprised a coated microprojection array device, adhered to the center of a LDPE backing with an adhesive (7 cm2 disc). Patches were remained on the skin for 1 h (n=4-5). A group of animals (n=5) received an intravenous injection of 22 μg hPTH(1-34) instead of the microprojection array. Blood samples were collected through the carotid catheter at time intervals following patch application or IV injection. All blood samples were centrifuged immediately for plasma collection, which was then stored at −80° C. until analysis. Plasma hPTH(1-34) was determined by the EIA, a commercial enzyme immunoassay kit for hPTH (1-34) from Peninsula Lab. (San Carlos, Calif.). The hPTH (1-34) dose delivered by microprojection arrays was extrapolated based on the area under the curve (AUC) calculation compared to IV administration of hPTH(1-34).

Figure 9:
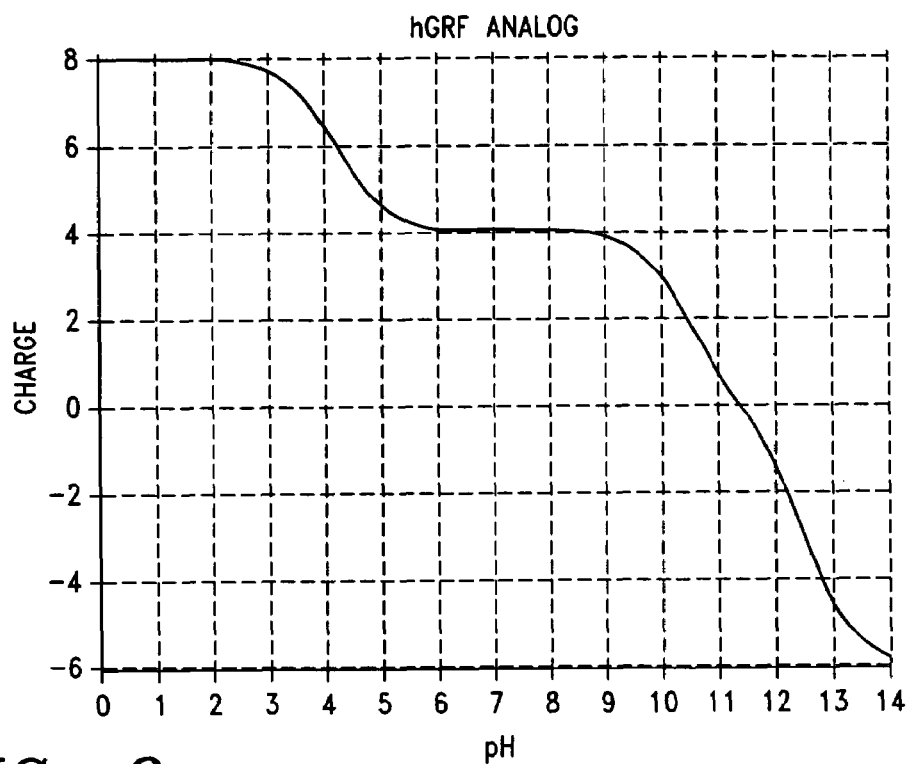
FIG. 9 is a graph showing the charge profile of a peptide comprising a hGRF analog.

Results are shown in Table 1, which demonstrate that different amounts of HPTH(1-34) were delivered from each solid formulation. The solid formulations containing only hPTH(1-34) acetate (No. 1 and 2) delivered less than 2 μg on average. Addition of non-volatile counterions to hPTH(1-34) acetate increased delivery significantly to up to 11.2 μg after the addition of the non-volatile counterion glycolic acid (No. 5). The two other non-volatile counterions tested, tartaric (No. 6) and hydrochloric acid (Nos. 3 and 4) also increased hPTH(1-34) delivery.

for one mole of peptide there are 6.5 moles of acetic acid. At pH 5, the peptide presents about 4.5 positive charges (see FIG. 9), leaving 2 moles of free acetic acid per mole of peptide. After storage for 3 months at ambient conditions the number of moles of acetate per mole of peptide decreases to 3.8, demonstrating depletion of the volatile counterion from the coating. Extrapolation from the charge profile of FIG. 9 shows that reconstitution of the coating in water would yield a pH 9.5 solution, which represents a dramatic increase in pH from the pH of the initial solution.

TABLE 2

Acetate/hGRF analog mole ratio in Ti coated samples

| Sample | Storage condition | Drug content (μg/cm2) | Average coating thickness (μm) | Acetate/peptide mole ratio (Initial = 6.5) |
|---|---|---|---|---|
| Ti disc | 3 monthsRoom temperature $N^2$ atmosphere | 384 | 3.8 | 3.8 ± 0.1 |

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition comprising a formulation of a pharmaceutically active agent, a volatile counterion and a non-vola-

TABLE 1

PTH formulations and hPTH(1-34) delivery in the hairless guinea pig

| No | Formulation solution (wt %) | Ratio (hPTH(1-34):Acetate:non-volatile counterion) | Amount of hPTH(1-34) coated on array (μg) ± SD | Amount delivered (μg) ± SD |
|---|---|---|---|---|
| 1 | 21.2% hPTH(1-34), 3.8% acetic acid, water q.s. | 1:3:0 | 28.0 ± 6.6 | 1.1 ± 1.1 |
| 2 | 21.2% hPTH(1-34), 3.8% acetic acid, water q.s | 1:3:0 | 35.0 ± 11.4 | 1.5 ± 1.7 |
| 3 | 22.3% hPTH(1-34), 2.7% acetic acid, 0.4% HCl, water q.s. | 1:2:2 | 40.0 ± 9.8 | 5.9 ± 2.5 |
| 4 | 16.2% hPTH(1-34), 3.8% acetic acid, 0.5% HCl, 20.2% excipients, water q.s. | 1:3:3 | 30.5 ± 2.3 | 6.1 ± 4.0 |
| 5 | 6.2% hPTH(1-34), 3.8% acetic acid, 2.1% glycolic acid, 12.2% excipients, water q.s. | 1:3:4 | 45.9 ± 11.7 | 11.2 ± 2.7 |
| 6 | 16.2% hPTH(1-34), 3.8% acetic acid, 1.2% Tartaric acid, 20.23% excipients, water q.s. | 1:3:2 | 29.0 ± 4.3 | 4.2 ± 1.5 |

Example 3

In order to demonstrate depletion of coatings containing volatile counterions, we coated 1 cm² titanium disc with a pH 5 aqueous formulation made by solubilizing 20 wt % of the acetate form of a peptide, an hGRF analog. Following coating, each disc was stored under 20 mL nitrogen atmosphere at room temperature for 3 months.

Results in Table 2 compare the acetate/peptide mole ratio at the initial and the 3 month time points. At the initial time point tile counterion, wherein said pharmaceutically active agent is hPTH(1-34) present as uncharged species and as charged species and wherein said non-volatile counterion is present in an amount sufficient to achieve a molar ratio between said uncharged species and charged species of about 1 uncharged species to at least 100 charged species; wherein said formulation has increased pH stability and solubility when dried, and wherein said composition is applied to a transdermal delivery device having stratum corneum-piercing microprojections; wherein said composition achieves an increase in delivery of the pharmaceutically active agent compared to a composition comprising a formulation without said non-volatile counterion.

2. The composition of claim 1, wherein said formulation has a pH, said pharmaceutically active agent has a positive charge at said formulation pH and said non-volatile counterion comprises a strong acid.

3. The composition of claim 2, wherein said strong acid has at least one pKa lower than about 2.

4. The composition of claim 3, wherein said strong acid is selected from the group consisting of hydrochloric acid, hydrobromic acid, nitric acid, sulfonic acid, sulfuric acid, maleic acid, phosphoric acid, benzene sulfonic acid and methane sulfonic acid.

5. The composition of claim 1, wherein said pharmaceutically active agent has a mole ratio between uncharged species and charged species of at least 1 to 100 at a pH between 4 and 10.

6. The composition of claim 1, wherein said composition achieves a five fold increase in delivery of the pharmaceutically active agent compared to a composition comprising a formulation without said non-volatile counterion.

7. A composition comprising a formulation of a pharmaceutically active agent, a volatile counterion and a non-volatile counterion, wherein said pharmaceutically active agent is hPTH (1-34) present as uncharged species and as charged species; wherein said pharmaceutically active agent has a positive charge at the pH of the formulation and said non-volatile counterion comprises a strong acid; and wherein said formulation has increased pH stability and solubility when dried.

8. The composition of claim 1, wherein the non-volatile counterion comprises a weak acid or a strong acid.

9. The composition of claim 8, wherein the weak acid is glycolic acid or tartaric acid.

10. The composition of claim 8, wherein the strong acid is hydrochloric acid.

11. The composition of claim 8, wherein hPTH(1-34) is present as an acetate salt.

12. A composition comprising a formulation of hPTH(1-34), a volatile counterion and a non-volatile counterion from a weak or strong acid, wherein said non-volatile counterion is present in an amount sufficient to achieve a molar ratio of about 1 uncharged hPTH species to at least about 100 charged hPTH species, wherein said composition achieves an increase in delivery of said hPTH when applied to a transdermal delivery device having stratum corneum-piercing microprojections compared to a composition comprising a formulation without said non-volatile counterion.

13. The composition of claim 12, wherein the weak acid is glycolic acid or tartaric acid.

14. The composition of claim 12, wherein the strong acid is hydrochloric acid.

15. The composition of claim 12, wherein hPTH(1-34) is present as an acetate salt.

* * * * *